US005942422A

United States Patent [19]
Rothstein

[11] Patent Number: 5,942,422
[45] Date of Patent: Aug. 24, 1999

[54] METHOD FOR GENERATING A DIRECTED, RECOMBINANT FUSION NUCLEIC ACID

[75] Inventor: Rodney Rothstein, Maplewood, N.J.

[73] Assignee: The Trustees of Columbia University in the City of New York, New York, N.Y.

[21] Appl. No.: 08/746,667

[22] Filed: Nov. 14, 1996

[51] Int. Cl.$^6$ ..................................... C12P 19/34
[52] U.S. Cl. .................... 435/91.1; 435/91.2; 435/172.3; 435/252.3; 435/320.1; 435/810; 935/17; 935/22; 935/66; 536/23.1; 536/25.3
[58] Field of Search .................. 435/91.1, 91.2, 435/172.3, 320.1, 252.3, 810; 536/23.1, 25.3; 935/22, 17, 66

[56] References Cited

U.S. PATENT DOCUMENTS

| | | |
|---|---|---|
| 5,270,170 | 12/1993 | Schatz et al. . |
| 5,338,665 | 8/1994 | Schatz et al. . |
| 5,427,908 | 6/1995 | Dower et al. . |
| 5,432,018 | 7/1995 | Dower et al. . |
| 5,469,530 | 11/1995 | Schatz et al. . |
| 5,482,845 | 1/1996 | Soares et al. . |
| 5,491,074 | 2/1996 | Aldwin et al. . |
| 5,512,463 | 4/1996 | Stemmer . |
| 5,521,077 | 5/1996 | Khosla et al. . |
| 5,525,486 | 6/1996 | Honjo et al. . |
| 5,541,061 | 7/1996 | Fodor et al. . |
| 5,565,332 | 10/1996 | Hoogenboom et al. . |

OTHER PUBLICATIONS

Jones et al., BioTechniques 12(4):528–533, 1992.
Klug et al., Nucleic Acids Research 19 (10):2793, 1991.
Vallejo et al., PCR Methods and Applications 4:S123–S130 (Cold Spring Harbor Laboratory), 1994.
Jones et al., Nature 344:793–794, Apr. 19, 1990.
Bendixen, C., S. Gangloff, and R. Rothstein, A yeast mating–selection scheme for detection of protein—protein interactions. Nucleic Acids Research, 1994. 22(9): pp. 1778–1779.

Chalfie, M., et al., Green fluorescent protein as a marker for gene expression. Science, 1994. 263(5148): pp. 802–805.

Choulika, A., et al., Induction of homologous recombination in mammalian chromosomes by using the I–SceI system of *Saccharomyces cerevisiae*. Molecular & Cellular Biology, 1995. 15(4): pp. 1968–1973.

Fields, S. and O. Song, A novel genetic system to detect protein—protein interactions. Nature, 1989. 340(6230):pp. 245–246.

Fischer, S.G. et al. A high–resolution annotated physical map of the human chromosome 13q12–13 region containing the breast cancer susceptibility locus BRCA2. Proceedings of the National Academy of Sciences of the United States of America, 1996. 93(2): pp. 690–694.

(List continued on next page.)

*Primary Examiner*—Stephanie W. Zitomer
*Attorney, Agent, or Firm*—John P. White; Cooper & Dunham LLP

[57] ABSTRACT

The present invention provides for a method for generating a directed, recombinant fusion nucleic acid molecule which includes: (A) contacting a first pair of single-stranded primers with a first strand and a second strand of a first nucleic acid molecule and a second pair of single-stranded primers with a first strand and a second strand of a second nucleic acid molecule under hybridization conditions, (B) amplifying the first nucleic acid molecule and the first pair of primers and the second nucleic acid molecule and the second pair of primers under amplification conditions, separately; (C) mixing the amplification products from step (B) and the first primer of the first pair of primers and the second primer of the second pair of primers under hybridization conditions; (D) amplifying the hybridized molecules of step (C) under amplification conditions so as to generate a directed, recombinant fusion nucleic acid molecule so as to generate a directed, recombinant fusion nucleic acid molecule.

35 Claims, 19 Drawing Sheets

OTHER PUBLICATIONS

Gangloff, S., et al., The yeast type I topoisomerase Top 3 interacts with Sgs1, a DNA helicase homolog: a potential eukaryotic reverse gyrase. Molecular & Cellular Biology, 1994. 14(12): pp. 8391–8398.

Kostriken, R., et al., A site–specific endonuclease essential for mating–type switching in *Saccharomyces cerevisiae*. Cell, 1983. 35(1): pp. 167–174.

Kunes, S., D. Botstein, and M.S. Fox, Synapsis–mediated fusion of free DNA ends forms inverted dimer plasmids in yeast. Genetics, 1990. 124(1): pp. 67–80.

Ma, H., et al., Plasmid construction by homologous recombination in yeast. Gene, 1987. 58(2–3): pp. 201–216.

Orr–Weaver, T.L., J.W. Szostak, and R.J. Rothstein, Yeast transformation: a model system for the study of recombination. Proceedings of the National Academy of Sciences of the United States of America, 1981. 78(10): pp. 6354–6358.

Plessis, A., et al., Site–specific recombination determined by I–SceI, a mitochondrial group I intron–encoded endonuclease expressed in the yeast nucleus. Genetics, 1992. 130(3): pp. 451–460.

Rose, M., P. Grisafi, and D. Botstein, Structure and function of the yeast URA3 gene: expression in *Escherichia coli*. Gene, 1984. 29(1–2): pp. 113–124.

Rothstein, R.J., One–step gene disruption in yeast. Methods in Enzymology, 1983. 101: pp. 202–211.

Shuster, J.R., D. Moyer, and B. Irvine, Sequence of the *Kluyveromyces lactis* URA3 gene. Nucleic Acids Research, 1987. 15(20): p. 8573.

Spencer, F., et al., Yeast kar1 mutants provide an effective method for YAC transfer to new hosts. Genomics, 1994. 22(1): pp. 118–126.

Thomas, B.J. and R. Rothstein, Elevated recombination rates in transcriptionally active DNA. Cell, 1989. 56(4): pp. 619–630.

Gaillardin, M. Maftahi and J–M Nicaud. (1996) "Sticky–End Polymerase Chain Reaction Method for Systematic Gene Disruption in *Saccharomyces cerevisiae*," Yeast 12: 859–868 (Exhibit 2).

Mallet, Laurent and Michel jacquet. (1996) "Intergenic Flip Flop, a Method for Systematic Gene Disruption and Cloning in Yeast," Yeast 12: 1351–1357 (Exhibit 3).

FIG. 5

```
             R   G   S   E   F   Q   Q   E   F   G   T   R
Adaptamer A₁ 5'-cga gga tcc gaa ttc cag CAA GAA TTC GGC ACG AGG-3'

R   G   S   E   F   Q   P   R   I   R   H   E
Adaptamer A₂ 5'-cga gga tcc gaa ttc cag cCA AGA ATT CGG CAC GAG G-3'

R   G   S   E   F   Q   A   K   N   S   A   R
Adaptamer A₃ 5'-cga gga tcc gaa ttc cag gcC AAG AAT TCG GCA CGA GG-3'

Adaptamer B  5'-gttgaagtgaacttgcggGACGTTGTAAAACGACGG-3'
```

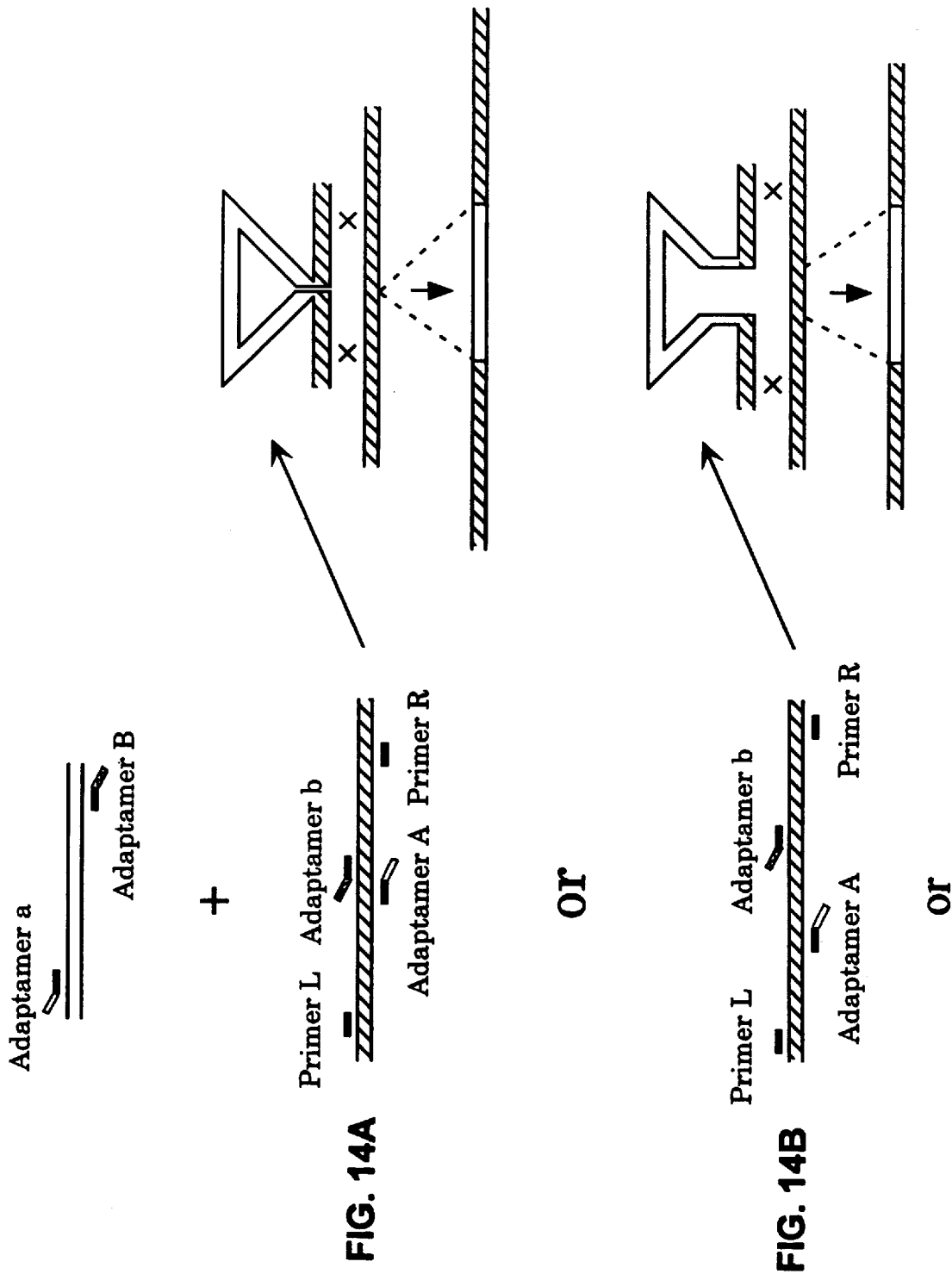

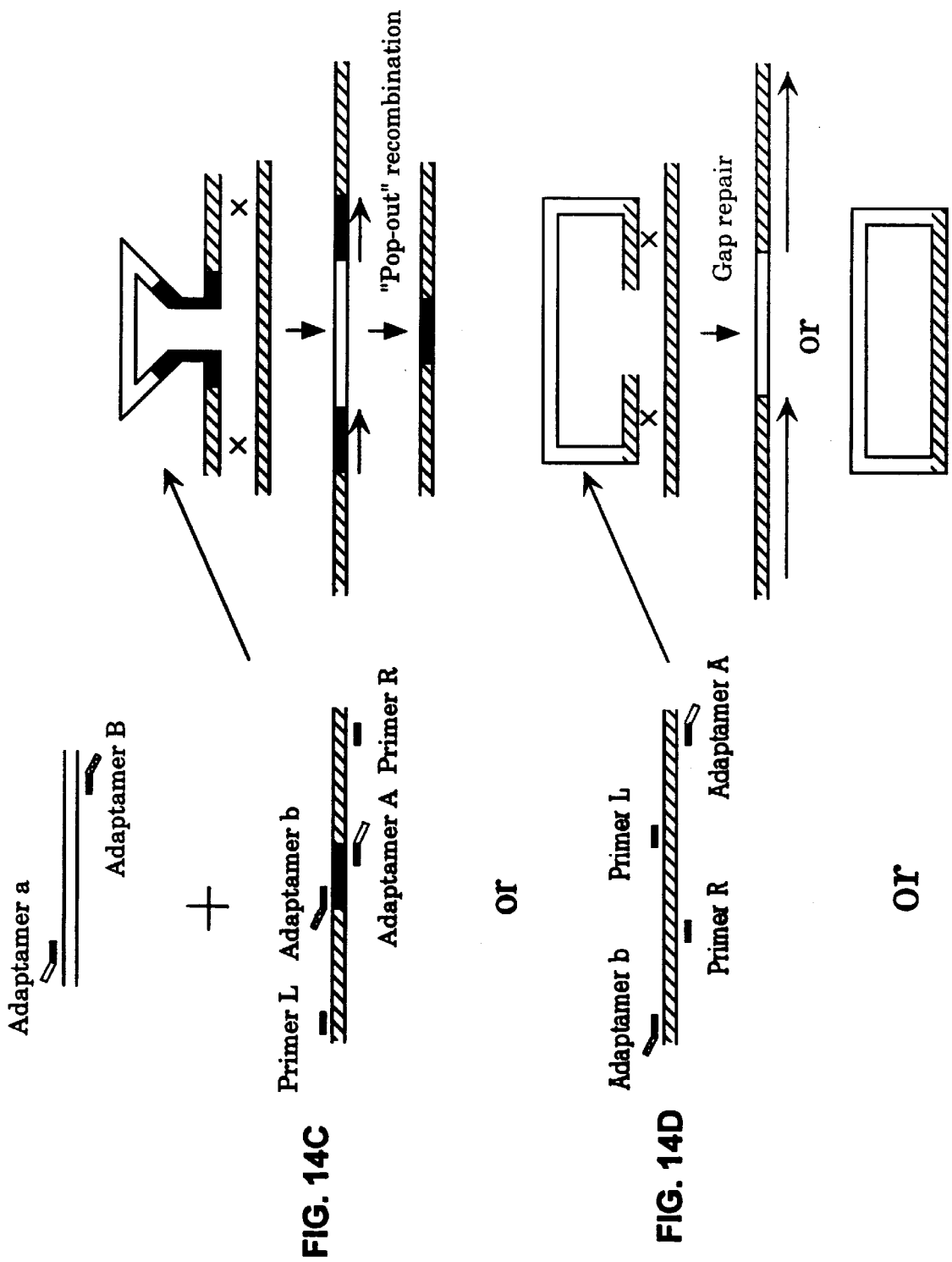

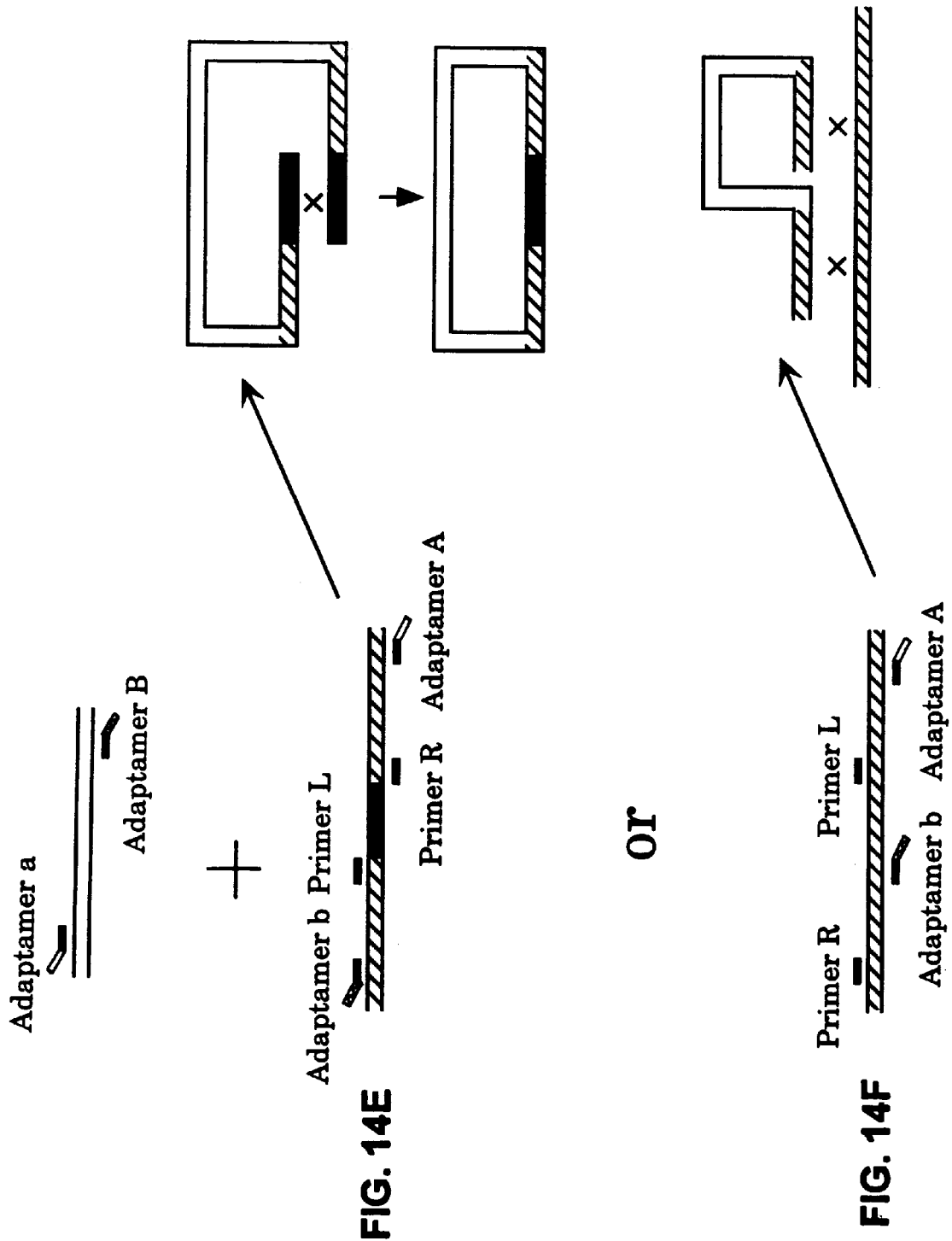

FIG. 15
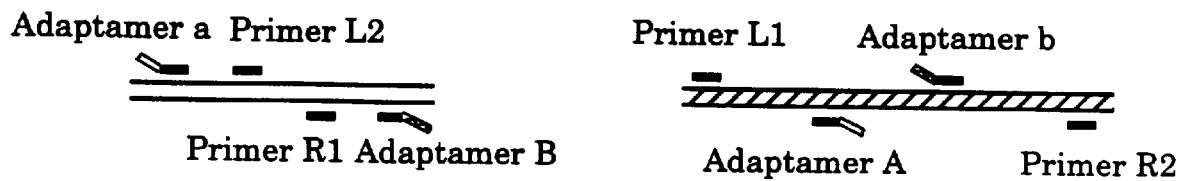
Adaptamer a  Primer L2          Primer L1    Adaptamer b
Primer R1 Adaptamer B          Adaptamer A    Primer R2
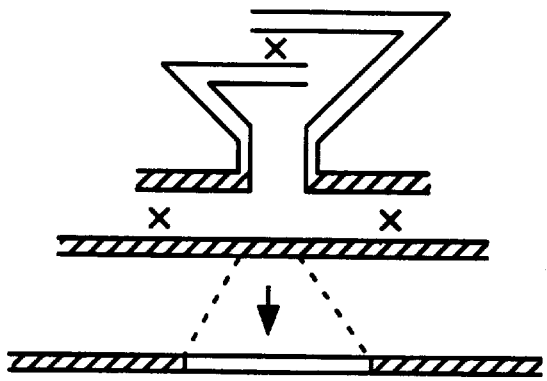
Also
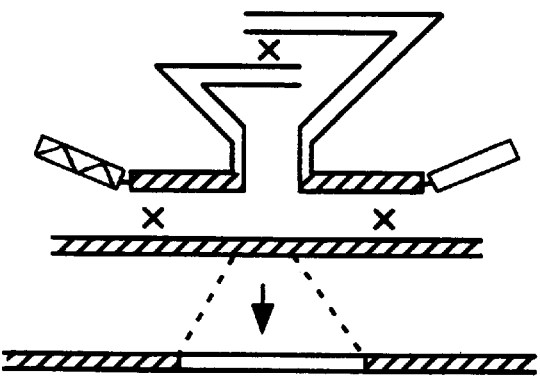

FIG. 17A
FIG. 17B
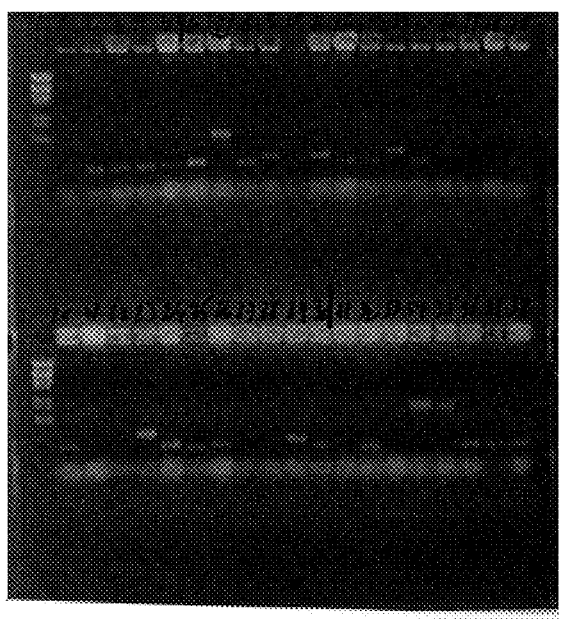

5,942,422

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CGAGGATCCG AATTCCAGCA AGAATTCGGC ACGAGG      36

(2) INFORMATION FOR SEQ ID NO:2:

```
        (i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

CGAGGATCCG AATTCCAGCC AAGAATTCGG CACGAGG                                  37

(2) INFORMATION FOR SEQ ID NO:3:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

CGAGGATCCG AATTCCAGGC CAAGAATTCG GCACGAGG                                 38

(2) INFORMATION FOR SEQ ID NO:4:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GTTGAAGTGA ACTTGCGGGA CGTTGTAAAA CGACGG                                   36
```

METHOD FOR GENERATING A DIRECTED, RECOMBINANT FUSION NUCLEIC ACID

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Attention of research scientists has recently focused upon various methods of creating libraries. The use of libraries is widespread in research and in the pharmaceutical industry. Libraries may consist of nucleic acid, peptides or even virtual molecules on a computer-readable material. Methods for the creation of libraries that are representative of the desired entity and that are useable has been a long felt challenge. In general, library construction has entailed many steps before the production of a final, useable library.

The following U.S. Patents are hereby incorporated by reference into this application in order to more fully describe the state of the art as known to one of ordinary skill in the art. U.S. Pat. No. 5,498,530, Peptide Library and Screening Method; U.S. Pat. No. 5,491,074 Association Peptides; U.S. Pat. No. 5,432,018 Peptide Library and Screening Systems; U.S. Pat. No. 5,427,908 Recombinant Library Screening Methods; U.S. Pat. No. 5,338,665 Peptide Library and Screening Method; U.S. Pat. No. 5,270,170 Peptide Library and Screening Method; U.S. Pat. No. 5,541,061 Methods for Screening Factorial Chemical Libraries; U.S. Pat. No. 5,482,845, Method for Construction of Normalized cDNA Libraries; U.S. Pat. No. 5,512,463, Enzymatic inverse polymerase chain reaction library mutagenesis.

There are also peptide libraries and chimeric libraries that have been described. For example, see U.S. Pat. No. 5,525,486, Process for constructing cDNA library, and novel polypeptide and DNA coding for the same; U.S. Pat. No. 5,565,332, Production of chimeric antibodies—a combinatorial approach; U.S. Pat. No. 5,521,077, Method of Generating Multiple Protein Variants and Populations of Protein Variants Prepared thereby; U.S. Pat. No. 5,324,663, Methods and Products for the Synthesis of oligosaccharide structure on glycoproteins, glycolipids, or as free molecules, and for the isolation of cloned genetic sequences that determine these structures.

There have been combinatorial libraries also described which are usually composed of organic molecules attached to a solid support. A recent description of recently published patent applications may be found in Nature Biotechnology, Vol 14:1028–1029. Therein, the following published patent applications and patents were listed and described: Patent No. GB 2295152 A, solid phase synthesis of chemical library on flat solid support sheets divided into identifiable reaction zones; WO 9612014 A, repertoire of oligonucleotide tags comprise molecular tagging system used to track identify and sort molecules; WO 9607754, Oligonucleotides for inducing mutagenesis in an Ig light chain CDR; WO 9603424 A, combinatorial library comprising Diels-Alder products easily functionalized to form peptidomimetics for treating, e.g. Parkinson's disease; WO 9603418 A, Soluble combinatorial library by solid phase synthesis by using soluble polymeric support for core molecule attachment and buildup; WO 9603212 A, multidimensional device for synthesis of combinatorial chemical libraries comprising stacked trays of synthesis cells supplied with substrates and reagents.

SUMMARY OF THE INVENTION

The present invention provides for a method for generating a directed, recombinant fusion nucleic acid molecule which comprises: (a) contacting a first pair of single-stranded primers with a first strand and a second strand of a first nucleic acid molecule and a second pair of single-stranded primers with a first strand and a second strand of a second nucleic acid molecule under hybridization conditions, wherein the primers are suitable for use in a polymerase chain reaction, and (i) the first primer of the first pair of primers comprises a sequence that is homologous to the first strand of the first nucleic acid molecule; (ii) the second primer of the first pair of primers comprises a 3' sequence that is homologous to the second strand of the first nucleic acid molecule and a 5' sequence; (iii) the first primer of the second pair of primers comprises a 3' sequence homologous to the first strand of the second nucleic acid molecule and a 5' sequence that is complementary to the 5' sequence of the second primer of the first pair of primers, and (iv) the second primer of the second pair of primers comprises a sequence that is homologous to the second strand of the second nucleic acid moleucle; (b) amplifying the first nucleic acid molecule and the first pair of primers and the second nucleic acid molecule and the second pair of primers under amplification conditions, separately; (c) mixing the amplification products from step (b) and the first primer of the first pair of primers and the second primer of the second pair of primers under hybridization conditions; (d) amplifying the hybridized molecules of step (c) under amplification conditions so as to generate a directed, recombinant fusion nucleic acid molecule.

BRIEF DESCRITION OF THE FIGURES

FIG. 1. A sample region of the yeast genome is shown. Arrows indicate open reading frames (ORFs) and the direction of transcription. YCL26C is 357 base pairs in length. The length of the adaptamers shown are not to scale.

FIG. 2. Schematic diagram of the experiment to demonstrate the feasibility of PCR/recombination-directed library construction.

FIG. 3. Ethidium bromide stained gel electrophoresis of three reactions used to create the PCR/recombination substrate described in FIG. 2. Lane 1 shows the product of a reaction where the three fragments (Adj-A, $SGS_{1-795}$, and Adj-B) were mixed in a 1:1:1 ratio prior to gel purification. Lanes 2 and 3 show the products obtained using purified fragments mixed in a 1:2:1 and a 1:4:1 ratio, respectively.

FIG. 4. Sixteen transformants were analyzed by colony PCR using primers L and R to determine the insert size. The smaller band indicates a single example that does not contain an insert.

FIG. 5. Four adaptamers are shown for generating EST fragments from sequences cloned in pT7T3D. For all four, the first 18 lower case letters are sequences homologous to pGAD10. For adaptamer $A_1$, (Seq. I.D. No. 1) the next 18 upper case letters are homologous to the EcoRI linker added to the cDNAs before cloning into the pT7T3D vector used by I.M.A.G.E. Adaptamer $A_2$ (Seq. I.D. No. 2) and adaptamer $A_3$ (Seq. I.D. No. 3) have one and two extra nucleotides, respectively between this sequence. The 18 upper case letters in adaptamer B (Seq I.D. No. 4) are homologous to sequences adjacent to the NotI linker used to prime the synthesis of the cDNA. After PCR with this set of adaptamers, one of the three will result in an in-frame fusion to the EST. The amino acids displayed above the nucleotide sequences of Adaptamers $A_1$, $A_2$ and $A_3$ represent the linker between the EST and the activation domain of Gal4 after successful recombination cloning.

FIG. 6. Use of the four adaptamers shown in FIG. 5 to create an in-frame fusion to a cloned EST. The adaptamers are homologous to sequences outside of the cloned EST. The amplified products are extended by a second round of PCR using Adj-A and Adj-B in the presence of excess primers L and R. The three PCR/recombination substrates are co-transformed with linearized pGAD10 to create the three different clones. Only one of the three clones is fused in-frame with the Gal4 activation domain.

FIG. 7. An outline of the basic steps for making a promoter fusion library using PCR/recombination. The flag indicates the promoter region of the "fragment of interest" (FOI).

FIG. 8. Illustration of the procedure for kar1-mediated plasmid transfer of a portable promoter fusion library.

FIG. 9. An outline of a construction of a portable gene disruption library.

FIG. 10. I-SceI induction of homologous recombination. The primers shown as arrows in the marker are used to confirm correct integration in combination with the adaptamer B.

FIG. 11. An illustration of the procedure for kar1-mediated plasmid transfer of a portable gene disruption library.

FIG. 12. An illustration of the generation of a directed, fusion recombinant double-stranded nucleic acid molecule. Two polymerase chain reactions (PCRs) are carried out. (1) Primer L and adaptamer A hybridizing to the left (stippled) nucleic acid and generating a PCR product with the right end refecting the sequence of the 5' sequence of adaptamer A. (2) Primer R and adaptamer a hybridizing to the right nucleic acid molecule and producing a product nucleic acid with the left end sequence homologous to the 5' sequence of adaptamer a. The original nucleic acid molecules may be either linear or circular. Adaptamer A and adaptamer a have complementary 5' end sequences. The linear products from (1) and (2) are then mixed together with primer L and primer R and undergo PCR with normal denaturation, hybridization, extension and elongation steps. This final PCR produces at least one nucleic acid which is a directed, fusion recombinant nucleic acid product.

FIG. 13. An illustration of the generation of a directed, fusion recombinant double-stranded nucleic acid molecule. Three separate PCRs are carried out with each pair of primers as shown in order to generate at least three linear products as shown. The original nucleic acid molecules may be linear or circular. Each linear product has incorporated the 5' sequence end of the original adaptamer thereby allowing overlap and extension to be possible. The linear products from the three primary PCRs are mixed together with primer R and primer L and undergo normal PCR (denaturation, hybridization, extension and elongation). The second PCR produces at least one linear product that is a fusion of the three original nucleic acid molecules. The placement of the adaptamers allows one to engineer the location of each original nucleic acid and the orientation or direction of each nucleic acid in relation to the others. This procedure may be modified to utilize many more nucleic acid molecules. For example one may begin with four original nucleic acids, or five or six or thousands.

FIGS. 14A, 14B, 14C, 14D, 14E and 14F. Description of some possible uses of adaptamers in the generation of directed, fusion recombinant nucleic acid molecules. There exist other uses of the adaptamers and the generation of directed, fusion recombinant nucleic acid molecules which are not depicted here.

FIG. 14A. Insertion. The use of adaptamers to orient and insert a foreign piece of nucleic acid into a region of an existing target nucleic acid. A first PCR of the foreign piece of nucleic acid and appropriate adaptamers is done in order to generate a product with ends receptive to overlap and connectivity with the target nucleic acid. The target nucleic acid is separately hybridized to two sets of primers as shown which are also adaptamers with complementary 5' sequences to the adaptamers used with the foreign nucleic acid. Adaptamer b and adaptamer A are predefined so that the 3' sequence of adaptamer b is complementary to the target nucleic acid adjacent to the region which is complementary to the 3' sequence of adaptamer A. Thus, the products from both PCRs may be mixed and again undergo PCR in order to generate the striped-&-white block product shown on the right of the figure. This product can then be mixed with the target nucleic acid under appropriate recombination conditions. Recombination would then occur and produce the final product shown: the target nucleic acid with the foreign nucleic acid inserted in the predetermined region. The region of insertion may be determined a priori and the adaptamers can be engineered based on the sequences surrounding the predefined insertion point.

FIG. 14B. Simultaneous insertion and deletion. The foreign nucleic acid is hybridized with predefined adaptamers as shown and described above. However, the 5' end sequence of the adaptamers are now engineered to reflect two sequences of the target nucleic acid some distance from each other.

FIG. 14C. An insertion accompanied by a duplication is depicted. Such a product may be obtained if the sequences projected for amplification from each pair of primers (primer L/adaptamer A and adaptamer b/primer R) cross one another upon amplification. The black box in the left hand drawing is the region that would be amplified by both sets of primers. The black boxes on the right side of the arrow indicate the same region shown as a duplication after the first recombination event. The white region depicts the foreign nucleic acid as in FIGS. 14A and 14B above. After the first recombination event, a second event (depicted "pop-out" recombination) can generate a single black region.

FIG. 14D. Gap repair. In this case, the engineering of the predefined adaptamers can create a gap or anomaly in the target sequence which can subsequently be repaired into a linear duplication or an intact circle.

FIG. 14E. Another example of engineered adaptamers used to create a duplication on the ends of the molecule such that recombination results in a circular molecule.

FIG. 14F. Another example of engineered adaptamers to carry out recombination that results one or two linear molecules whose ends include the amplified sequences.

FIG. 15. Use of adaptamers to effect insertion of long foreign nucleic acid molecules into a target nucleic acid molecule and a coincident deletion.

FIG. 16. Two nucleic acid molecules capable of cross-over recombination with four different counter-selectable markers on each end of each nucleic acid molecule. Thus, one is capable of selecting against these four markers and thus selecting for a more rare, correct cross-over event.

FIG. 17A and 17B. Ethidium bromide stained products separated via gel electrophoresis. The bands shown are products derived from the methods described herein wherein the foreign nucleic acid and the target nucleic acid were derived from an mRNA or a cDNA.

DETAILED DESCRIPTION OF THE INVENTION

Figure 1:
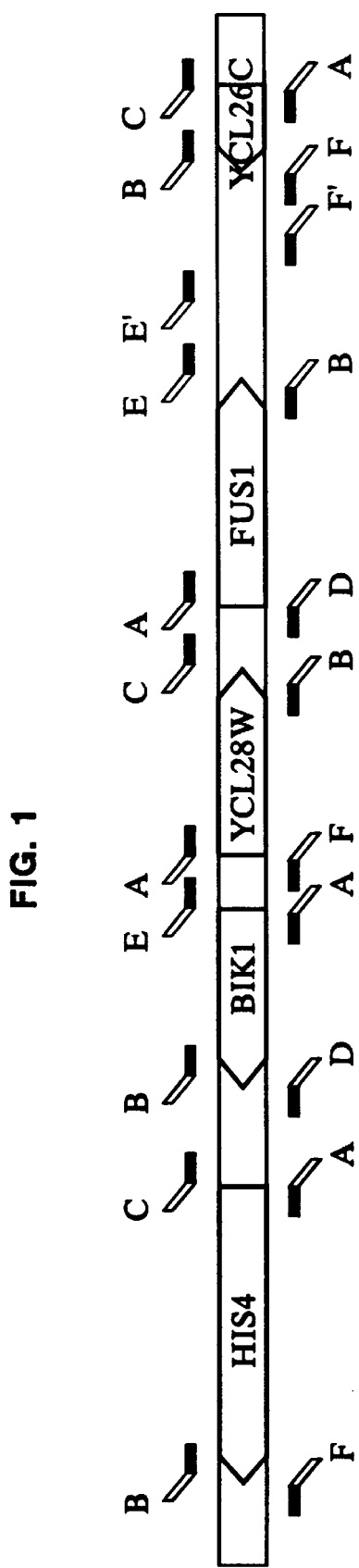

The present invention provides for a method for generating a directed, recombinant fusion nucleic acid molecule which comprises: (a) contacting a first pair of single-stranded primers with a first strand and a second strand of a first nucleic acid molecule and a second pair of single-stranded primers with a first strand and a second strand of a second nucleic acid molecule under hybridization conditions, wherein the primers are suitable for use in a polymerase chain reaction, and (i) the first primer of the first pair of primers comprises a sequence that is homologous to the first strand of the first nucleic acid molecule; (ii) the second primer of the first pair of primers comprises a 3' sequence that is homologous to the second strand of the first nucleic acid molecule and a 5' sequence; (iii) the first primer of the second pair of primers comprises a 3' sequence homologous to the first strand of the second nucleic acid molecule and a 5' sequence that is complementary to the 5' sequence of the second primer of the first pair of primers, and (iv) the second primer of the second pair of primers comprises a sequence that is homologous to the second strand of the second nucleic acid moleucle; (b) amplifying the first nucleic acid molecule and the first pair of primers and the second nucleic acid molecule and the second pair of primers under amplification conditions, separately; (c) mixing the amplification products from step (b) and the first primer of the first pair of primers and the second primer of the second pair of primers under hybridization conditions; (d) amplifying the hybridized molecules of step (c) under amplification conditions so as to generate a directed, recombinant fusion nucleic acid molecule.

The method may be repeated and the directed, recombinant fusion nucleic acid molecule generated may include another first nucleic acid molecule. The first nucleic acid molecule may include a cDNA molecule, a genomic nucleic acid molecule, a mitochondrial nucleic acid molecule, a chromosomal nucleic acid molecule, a synthetic nucleic acid molecule or an extra-chromosomal nucleic acid molecule. The first nucleic acid molecule may be derived from an mRNA, a single-stranded DNA, a biological sample or a single-stranded cDNA. The biological sample may include cerebrospinal fluid, blood, plasma, ascites fluid, tissue, urine, sputum, feces, hair, amniotic fluid, saliva, lung lavage, or cell extracts.

Each primer may include from about 4 nucleotides in length to about 200 nucleotides in length. Each primer may include from about 25 nucleotides in length to about 80 nucleotides in length. The first or second nucleic acid molecule or the primers may be synthesized de novo.

The present invention also provides for a method for generating a directed, recombinant fusion nucleic acid molecule capable of cross-over recombination which comprises: (A) contacting (i) a first pair of single-stranded primers with a first strand and a second strand of a first nucleic acid molecule, and (ii) a first single-stranded primer of a second pair of primers with a second nucleic acid molecule having two ends, wherein a first end is homologous to a portion of a fourth double-stranded nucleic acid molecule; (iii) a second single-stranded primer of the second pair of primers with a third nucleic acid molecule having two ends, wherein a first end is homologous to a second portion of the fourth double-stranded nucleic acid molecule, wherein the first and second pair of primers are suitable for use in a polymerase chain reaction, and (a) the first primer of the first pair comprises a 3' sequence that is homologous to the first strand of the first nucleic acid molecule and a 5' sequence that is homologous to the second end of the second double-stranded nucleic acid molecule; (b) the second primer of the first pair of primers comprises a 3' sequence that is homologous to the second strand of the first nucleic acid molecule and a 5' sequence that is homologous to the second end of the third double-stranded nucleic acid molecule; (c) the first primer of the second pair of primers comprises a sequence that is homologous to a first strand within the first end of the second nucleic acid molecule, and (d) the second primer of the second pair of primers comprises a sequence that is homologous to the second strand within the first end of the third nucleic acid molecule; (B) amplifying the first nucleic acid molecule and the first pair of primers, and the second and third nucleic acid molecules and the second pair of primers under amplification conditions so as to generate a directed, recombinant fusion nucleic acid molecule capable of cross-over recombination with the fourth double-stranded nucleic acid.

The method may be repeated and the directed, recombinant fusion nucleic acid molecule generated comprises another first nucleic acid molecule. The first nucleic acid molecule may include a cDNA molecule, a genomic nucleic acid molecule, a mitochondrial nucleic acid molecule, a chromosomal nucleic acid molecule, a synthetic nucleic acid molecule or an extra-chromosomal nucleic acid molecule. The first nucleic acid molecule may be derived from an mRNA, a single-stranded DNA, a biological sample or a single-stranded cDNA. The fourth nucleic acid molecule may include a replicable vector. The replicable vector may include a retroviral vector, a phage vector, an expression vector, a self-replicating vector, a viral vector, a plasmid vector, a phagemid vector, or a YAC vector. The second and the third nucleic acid molecules may be synthesized de novo.

The present invention may also provide for a method for generating a directed, recombinant fusion nucleic acid molecule capable of cross-over recombination which comprises: (A) contacting (i) a first pair of single-stranded primers with a first strand and a second strand of a first nucleic acid molecule; (ii) a second and a third pair of primers with a second nucleic acid molecule having a first strand and a second strand, wherein the primers are suitable for use in a polymerase chain reaction, and (a) the first primer of the first pair comprises a 3' sequence that is homologous to the first strand of the first nucleic acid molecule and a 5' sequence; (b) the second primer of the first pair of primers comprises a 3' sequence that is homologous to the second strand of the first nucleic acid molecule and a 5' sequence; (c) the first primer of the second pair of primers comprises a sequence that is homologous to the second strand of the second nucleic acid molecule; (d) the second primer of the second pair of primers comprises a 3' sequence that is homologous to the first strand of the second nucleic acid molecule and a 5' sequence that is complementary to the 5' sequence of the first primer of the first pair of primers; (e) the first primer of the third pair of primers comprises a 5' sequence complementary to the 5' sequence of the second primer of the first pair of primers and a 3' sequence homologous to the second strand of the second nucleic acid molecule, and (f) the second primer of the third pair of primers comprises a sequence that is homologous to the first strand of the second nucleic acid molecule; (B) amplifying (1) the first nucleic acid molecules and the first pair of primers and (2) the second nucleic acid molecule and the second and third pairs of primers, so as to generate at least one linear double-stranded nucleic acid product from each reaction; (C) denaturing the products from step (B) so as to obtain single-stranded products; (D) contacting the single-stranded products from step (C) with the first primer of the second set of primers and the second primer from the third set of primers, under suitable hybridization conditions, and (E) amplifying the the single-stranded products from step (D) under suitable amplification conditions, so as to generate a fusion nucleic acid molecule capable of cross-over recombination.

The cross-over recombination may occur in an appropriate host cell. The host cell may include a yeast cell, a mammalian cell, an *E. coli* cell, a eukaryotic cell, a prokaryotic cell, a plant cell, an insect cell, a slime mold cell. The first nucleic acid molecule may include a cDNA molecule, a genomic nucleic acid molecule, a mitochondrial nucleic acid molecule, a chromosomal nucleic acid molecule, a synthetic nucleic acid molecule or an extra-chromosomal nucleic acid molecule. The second nucleic acid molecule may include a replicable vector. The replicable vector may include a retroviral vector, a phage vector, an expression vector, a self-replicating vector, a viral vector, a plasmid vector, a phagemid vector, or a YAC vector. The fusion nucleic acid may include an insertion, a deletion a duplication or a mutation in the fusion nucleic acid molecule.

The present invention provides for a method for generating a directed, recombinant nucleic acid library which comprises: (A) contacting (i) a first pair of single-stranded primers with a first strand and a second strand of a first nucleic acid molecule; (ii) a second and a third pair of primers with a second nucleic acid molecule having a first strand and a second strand, wherein the primers are suitable for use in a polymerase chain reaction, and (a) the first primer of the first pair comprises a 3' sequence that is homologous to the first strand of the first nucleic acid molecule and a 5' sequence; (b) the second primer of the first pair of primers comprises a 3' sequence that is homologous to the second strand of the first nucleic acid molecule and a 5' sequence; (c) the first primer of the second pair of primers comprises a sequence that is homologous to the second strand of the second nucleic acid molecule; (d) the second primer of the second pair of primers comprises a 3' sequence that is homologous to the first strand of the second nucleic acid molecule and a 5' sequence that is complementary to the 5' sequence of the first primer of the first pair of primers; (e) the first primer of the third pair of primers comprises a 5' sequence complementary to the 5' sequence of the second primer of the first pair of primers and a 3' sequence homologous to the second strand of the second nucleic acid molecule, and (f) the second primer of the third pair of primers comprises a sequence that is homologous to the first strand of the second nucleic acid molecule; (B) amplifying (1) the first nucleic acid molecule and the first pair of primers and (2) the second nucleic acid molecule and the second and third pairs of primers, so as to generate at least one linear double-stranded nucleic acid product from each reaction; (C) denaturing the products from step (B) so as to obtain single-stranded products; (D) contacting the single-stranded products from step (C) with the first primer of the second set of primers and the second primer from the third set of primers under suitable hybridization conditions, and (E) amplifying the the single-stranded products from step (D) so as to generate a fusion nucleic acid molecule capable of cross-over recombination under suitable amplification conditions; (F) mixing the fusion nucleic acid molecule with the second nucleic acid molecule under suitable recombination conditions so as to generate a directed, recombinant nucleic acid library.

The library may include a two-hybrid library, an interaction library, a receptor library, a whole animal library, a tagged library, a chimeric library, a gene fusion library, a promoter trap library, an expression library, or a mutagenesis library.

The cross-over recombination may occur in an appropriate host cell. The host cell may include a yeast cell, a mammalian cell, an *E. coli* cell, a eukaryotic cell, a prokaryotic cell, a plant cell, an insect cell, a slime mold cell.

The present invention also may include a kit for generating a fusion nucleic acid based library which comprises: (a) a plurality of the adapted nucleic acid molecule primers; (b) reagents suitable to carry out a plurality of polymerase chain reactions, and (c) a replicable vector suitable for recombination.

The present invention provides for a method for generating a directed, recombinant fusion nucleic acid molecule capable of cross-over recombination which comprises: (A) providing for: (i) a first double-stranded nucleic acid molecule having a first strand and a second strand; (ii) a second double-stranded nucleic acid molecule having two ends, wherein a first end is homologous to a portion of a fourth double-stranded nucleic acid molecule; (iii) a third double-stranded nucleic acid molecule having two ends, wherein a first end is homologous to a second portion of the fourth double-stranded nucleic acid molecule; (iv) a first pair of primers and a second pair of primers suitable for use in a polymerase chain reaction, wherein, (a) a first primer of the first pair comprises a 3' sequence that is complementary to the first strand of the first nucleic acid molecule and a 5' sequence that is homologous to the second end of the second double-stranded nucleic acid molecule; (b) a second primer of the first pair of primers comprises a 3' sequence that is complementary to the second strand of the first nucleic acid molecule and a 5' sequence that is homologous to the second end of the third double-stranded nucleic acid molecule; (c) the first primer of the second pair of primers comprises a sequence that is complementary to a first strand within the first end of the second nucleic acid molecule, and (d) the second primer of the second pair of primers comprises a sequence that is complementary to the second strand within the second end of the third nucleic acid molecule; (B) performing extension, denaturation and hybridization steps of a polymerase chain reaction to generate at least one linear product from a mixture of the first, second and third nucleic acid molecules and the first and second pairs of primers so as to generate a directed, recombinant fusion nucleic acid molecule capable of cross-over recombination with the fourth double-stranded nucleic acid.

A method for generating a directed, recombinant fusion nucleic acid molecule capable of cross-over recombination which comprises: (A) providing for: (i) a first double-stranded nucleic acid molecule having a first strand and a second strand; (ii) a second double-stranded nucleic acid molecule having a first strand and a second strand; (iii) three pairs of primers suitable for use in a polymerase chain reaction, wherein, (a) a first primer of the first pair comprises a 3' sequence that is complementary to the first strand of the first nucleic acid molecule and a 5' sequence; (b) a second primer of the first pair of primers comprises a 3' sequence that is complementary to the second strand of the first nucleic acid molecule and a 5' sequence; (c) the first primer of the second pair of primers comprises a sequence that is complementary to the second strand of the second nucleic acid molecule, and (d) the second primer of the second pair of primers comprises a 3' sequence that is complementary to the first strand of the second nucleic acid molecule and a 5' sequence that is homologous to the 5' sequence of the first primer of the first pair of primers; (e) a first primer of the third pair of primers comprises a 5' sequence homologous to the 5' sequence of the second primer of the first pair of primers and a 3' sequence complementary to the second strand of the second nucleic acid molecule; (f) a second primer of the third pair of primers comprises a sequence that is complementary to the first strand of the second nucleic acid molecule; (B) performing extension, denaturation and hybridization steps of two polymerase chain reactions separately, comprising either: (1) the first and second nucleic acid molecules and the first and second pairs of primers and (2) the third nucleic acid molecule and the third pair of primers, or (3) the first and third nucleic acid molecules and the first and third pairs of primers and (4) the second nucleic acid molecule and the second pair of primers, so as to generate at least one linear nucleic acid product from each reaction; (C) performing extension, denaturation and hybridization steps of a polymerase chain reaction with the products from step (B) and the first primer of the second set of primers and the second primer from the third set of primers so as to generate a fusion nucleic acid molecule capable of cross-over recombination.

The present invention provides for the treatment of a nucleic acid sample or a biological sample to denature the double-stranded nucleic acid molecules and cause such hydrogen-bonded double-stranded molecules to become single-stranded. Such denaturing conditions may be heat, solvent, salt. The resulting nucleic acid molecules are then contacted with single-stranded oligonucleotide primers, the primers being capable of specifically hybridizing with pre-defined regions of the nucleic acid molecule and the primers being of a predefined sequence that is homologous to portions of other primers, under hybridizing conditions. Then, any nucleic acid molecules to which a pair of primers hybridizes are amplified so as to obtain a double-stranded amplification product. The amplification product may then be used in another denaturation and hybridization step with other nucleic acid molecules nd primers so as to produce a fusion, recombinant nucleic acid molecule.

Appropriate reaction conditions sufficient to permit specific hybridization and application through the following cycle include: denaturing the nucleic acid sequence; adding the primers and allowing them to hybridize to the appropriate strand of nucleic acid, primer extension products are formed from the primers and the nucleoside triphosphates, the extension products separate from the strands to become templates for the primers and new primer extension products are formed, wherein the hybridization, extension, and separation in the cycle occur at the appropriate temperature. (See U.S. Pat. No. 5,569,582, Rapid Amplification and Detection of Nucleic Acids.)

As used herein "amplification conditions" are those conditions under which a nucleic acid molecule may hybridize with two oligonucleotide primers which have some homology to the nucleic acid molecule and through primer extension replicate the nucleic acid molecule making a single-stranded nucleic acid molecule into a double stranded nucleic acid molecule via primer extension. This is elongation. The two strands are then melted apart by raising of the temperature and the single strands are again available for hybridization with a homologous single stranded oligonucleotide primer. Such conditions are well known to one of ordinary skill in the art and are described in more detail for certain specific nucleic acid molecules hereinbelow.

As used herein, "hybridization conditions" includes those temperatures, salt concentrations, primer sequences, nucleic acid sequences, solvent concentrations that allow two single-stranded nucleic acid molecules to base pair via hydrogen bonding as described by Watson and Crick. These conditions will be specific to each set of nucleic acids and primers. However, general conditions are well known to one of skill in the art and are described and referenced more fully hereinbelow.

As used herein "PCR" refers to a process of amplifying one or more specific nucleic acid sequences, wherein (1) oligonucleotide primers which determine the ends of the sequences to be amplified are annealed to single-stranded nucleic acid, (2) a nucleic acid polymerase extends the 3' ends of the annealed primers to create a nucleic acid strand complementary in sequence to the nucleic acid to which the primers were annealed, (3) the resulting double-stranded nucleic acid is denatured to yield two single-stranded nucleic acids, and (4) the processes of primer annealing, primer extension, and product denaturation are repeated enough times to generate easily identified and measured amounts of the sequences defined by the primers. Practical control of the sequential annealing, extension, and denaturation steps is exerted by varying the temperature of the reaction container, normally in a repeating cyclical manner. One of ordinary skill in the art would be aware of thermocycling machines which are available to automatically carry out the cycles of heating, cooling and heating. Annealing and extension occur optimally in the 40° C. to 80° C. temperature range (exact value depending on primer sequences, lengths, concentrations, salt concentrations, DMSO concentration, impurities in the reaction mixture), whereas denaturation requires temperatures in the 80° C. to 100° C. range (exact value depending on target sequence, target sequence length and concentration, salt concentration, DMSO concentration).

DNA amplification procedures by PCR are well known and are described in U.S. Pat. Nos. 4,683,195, 4,683,202, and 4,965,188, each of which is incorporated herein by reference. See *PCR Protocols: A Guide to Methods and Applications* [*PCR Protocols: A Guide to Methods and Applications.* (1990) Innis, M., Gelfand D., Sninsky, J. and White, T., eds., Academic Press, San Diego]. For ease of understanding the advantages provided by the present invention, a summary of PCR is provided. PCR requires two primers that are capable of hybridization with a single-strand of a double-stranded target nucleic acid sequence which is to be amplified. In PCR, this double-stranded target sequence is denatured and one primer is annealed to each single-strand of the denatured target. The primers anneal to the target nucleic acid at sites removed (downstream or upstream) from one another and in orientations such that the extension product of one primer, when separated from its complement, can hybridize to the extension product generated from the other primer and target strand. Once a given primer hybridizes to the target sequence, the primer is extended by the action of a DNA polymerase. DNA polymerase which is heat stable is generally utilized so that new polymerase need not be added after each denaturation step. Such thermostable DNA polyermase would be known to one of ordinary skill in the art, such as Taq polymerase. The extension product is then denatured from the target sequence, and the process is repeated. One particular method for minimizing the effects of cross contamination of nucleic acid amplification is described in U.S. Pat. No. 5,035,996, which are incorporated herein by reference. U.S. Pat. No. 5,494,810 Barany, Francis, et al. "Polymerase chain reaction (PCR)" refers to a patented process (described in U.S. Pat. Nos. 4,683,202 and 4,683,195) for the exponential amplification of a specific DNA fragment by utilizing two oligonucleotide primers that hybridize to opposite strands and flank the region of interest in a target DNA are hereby incorporated by reference. Also, those assays disclosed in the disclosures of U.S. Pat. No. 4,459,359 is hereby incorporated by reference.

The present invention provides for the use of adaptamers to design, fashion or manipulate fragments for PCR/ recombination-directed library construction. The present invention also provides for a method to connect non-contiguous fragments by using adaptamers for the construction of libraries by recombination.

In one embodiment the nucleic acid molecule is DNA, RNA or cDNA. In one embodiment, amplification is carried out using the polymerase chain reaction and a single or plurality of primer sets so as to provide PCR products of different lengths. In one embodiment, the plurality of primer sets are amplified together by PCR. In another embodiment, each primer set is amplified separately by PCR. The pairs of primers may be about 20 base pairs apart or may be about 5 kilobases apart and the polymerase chain reaction is carried out with more time allotted to elongation in the PCR profile of times and temperatures programmed into the temperature cycler. The primers may be any distance apart as long as the distance is capable of being replicated during one PCR cycle. This technology is constantly changing and the ability of polymerases is also being refined. Thus, the present invention provides for the use of any polymerase capable of such activity as producing 5 kilobases or more, i.e. 10, 20, 30, 50, 100 kilobases. The present invention also provides for the primers of a pair to be about 100 bases apart, about 300 bases apart, about 800 bases apart, about 1200 bases apart or about 1600 bases apart.

As used herein, "library" encompasses at least two nucleic acid molecules representative of a particular set or group of nucleic acids. The set or group may be a genome of a particular species; a genome of an individual animal, human or cell; a group of mutations in a nucleic acid molecule; a cDNA group; a group of cDNAs representative of genes which are expressed in a cell in response to a certain drug or signal; a group of cDNA's representative of genes expressed in a cell during a particular stage of development or differentiation; a group of cDNAs of a cell specific to a disorder or of an individual which has a particular disorder or disease; a set of nucleic acids that code for a ligand of a particular receptor; a set of nucleic acids that code for receptors of a particular ligand; a set of nucleic acids representative of genes which are expressed in a particular cell type (skin libraries, ovarian libraries, neural libraries); a set of nucleic acids that are representative of the genes that are expressed in one cell type and not in another cell type (i.e., a subtraction library). There are many other kinds of libraries which would be known to one of ordinary skill in the art.

The library may be a set of plasmids in a bacterial cell, or a set of DNAs in separate specific tubes or a set of strains of cells, yeast or prokaryotic or eukaryotic, that have been manipulated via DNA transformation to create gene disruptions, fusions deletions and insertions. The library may be a set of nucleic acids harbored in a host cell, or in a replicable vector in a host cell. In addition, circular vectors that can be subsequently manipulated (e.g. auto-digested) can be created. See FIGS. 7 and 8.

The present invention provides for the construction of 2-hybrid libraries, expression libraries, fusion libraries, promoter capture libraries, insertion libraries, rearrangement libraries, libraries representative of a genome. The genome may be derived from a human, a mouse, a frog, an insect, a horse, a pig, a monkey, a fish, a fowl, a mold, a bacterium, a mitochondrium, an archeological artifact.

The present invention may be carried out with either the target nucleic acid or the foreign nucleic acid linked to a solid support. The present invention may utilize automated steps or robotics.

DNA primer pairs of known sequence positioned 10–4,000 base pairs apart that are complementary to the plus and minus strands of the DNA to be amplified can be prepared by well known techniques for the synthesis of oligonucleotides. One end of each primer can be extended and may be modified to create restriction endonuclease sites when the primer is annealed to the target DNA. The PCR mixture may contain the target DNA, the DNA primer pairs, four deoxyribonucleoside triphosphates (A, T, C, G), $MgCl_2$, DNA polymerase (thermostable), and conventional buffers. The DNA can be amplified for a number of cycles (usually from 20–40 cycles). It is generally possible to increase the sensitivity of detection by using a multiplicity of cycles, each cycle consisting of a short period of denaturation of the target DNA at an elevated temperature, cooling of the reaction mixture, and polymerization with the DNA polymerase.

Choosing PCR primer sequences, preparing PCR reagents and reaction mixtures, and designing and running PCR are well known procedures in the PCR art. In the event that nucleic acid amplification is performed on suspended cells in a standard PCR tube, the cells are treated like any conventional PCR test sample: diluted into reaction mixture shortly before amplification is started, at a total cell number ranging from approximately 100 to approximately $10^6$. Enzyme, primers, target nucleic acid, dNTPs, $MgCl_2$ and buffer is mixed into a reaction mixture. After 50 to 100 $\mu$l of mineral oil have been added to the reaction tube, the tube is placed in a thermal cycler, many versions of which are commercially available from suppliers such as Perkin Elmer Cetus Instruments, and heated to a temperature between about 50° C. and about 80° C., preferably between 70° C. and 80° C.

If multiple samples are amplified simultaneously in different tubes, a fresh sampler tip is used to add the missing reagent(s) to each tube, to prevent cross-contamination. After all tubes have been prepared and capped, the standard three-temperature thermal cycle program of denaturation, annealing, and extension for approximately 10 to 40 cycles is performed under thermal cycler microprocessor control. Alternatively, and often preferably, a series of two-temperature cycles can be run wherein annealing and extension are performed at a single temperature, normally optimized for stringent annealing of primer to template. Because reaction rates may be somewhat retarded with cellular preparations as compared to cell-free nucleic acids, it may be necessary to increase the durations of the denaturation, anneal, extend, or anneal-extend cycle segments as much as several-fold from values standard when the test sample contains cell-free nucleic acid. This adjustment easily is performed by trial and error, looking for conditions which maximize the intensity of the signal seen during amplified nucleic acid detection or which minimize the number of cycles needed to reach a given signal intensity. A similar optimization procedure can be used for $MgCl_2$, dNTP, primer, and enzyme concentrations in the reaction mixture; these parameters often show different optima for different targets, and also may be affected when amplification occurs within fixed cells.

Primer pairs of known sequence positioned 10–300 base pairs apart that are complementary to the plus and minus strands of the DNA to be amplified can be prepared by well known techniques for the synthesis of oligonucleotides. Synthetic olionucleotides are well known to one of ordinary skill in the art and are available from companies such as Oligos, Etc.

Oligonucleotides for use as probes or PCR primers may be chemically synthesized according to the solid phase phosphoramidite triester method first described by Beaucage and Carruthers [Beaucage and Carruthers (1981) *Tetrahedron Lett.* 22:1859–1862] using an automated synthesizer, as described in Needham-VanDevanter [Needham-VanDevanter, D. R., et al., (1984) *Nucelic Acids Res.* 12:6159–61681]. Purification of oligonucleotides is by either native acrylamide gel electrophoresis or by anion-exchange HPLC as described in Pearson, J. D. and Regnier, F. E. [Pearson, J. D., and Regnier, F. E., (1983) *J. Chrom.* 255:137–14976.]. The sequence of the synthetic oligonucleotide can be verified using the chemical degradation method of Maxam, A. M. and Gilbert, W. [Maxam, A. M. and Gilbert, W. *Methods in Enzymology* (1980) Grossman, L. and Moldave, D., eds., Academic Press, New York, 65:499–560.].

The present invention also provides for computer programs that carry out the choice of primers for each particular target and foreign nucleic acid. Such computer program would utilize known nucleic acid sequences such as Genbank sequences or ATCC sequences in order to evaluate and choose the best primers for a particular purpose. The program would take into account the ultimate purpose or use of the primers or adaptamers and the region of interest of the target nucleic acid and the sequence and region of interest of the foreign nucleic acid. This computer program would be useful in designing adaptamers for the production of specific libraries and for the production of nucleic acids. The computer program would also be useful for antisense design and fusion protein design and gene therapy design.

As used herein, "amplification" is a special case of nucleic acid replication involving template specificity. It may be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be amplified or detected preferentially in the presence of other non-target nucleic acid sequences. Amplification techniques have been designed primarily for the detection of specific target sequences. Template specificity is achieved, in most amplification techniques, by the choice of enzyme. Amplification enzymes are enzymes that, under the conditions in which they are used, will process only specific sequences of nucleic acid in a heterogenous mixture of nucleic acid. For example, in the case of Q beta replicase, MDV-1 RNA is the specific template for the replicase. (See D. L. Kacian et al., Proc. Natl. Acad. Sci. USA 69:3038 (1972) at p.853 Abstract.) Other nucleic acids will not be replicated by this amplification enzyme. Similarly, in the case of T7 RNA polymerase, this amplification enzyme has a stringent specificity for its own promoters. (See M. Chamberlin et al., Nature 228:227 (1970) at p.229, col 2.)

In the case of T4 DNA ligase, the T4 ligase will not ligate the two oligonucleotides where there is a mismatch between the oligonucleotide substrate and the template at the ligation junction. (See D. Y. Wu and R. B. Wallace, Genomics 4:560 (1989).) Finally, Taq polymerase, by virtue of its ability to function at high temperature, is found to display high specificity for the sequences bounded and thus defined by the primers; the high temperature results in thermodynamic conditions that favor primer hybridization with the specific target sequences and not hybridization with non-target sequences. (See R. K. Saiki in PCR Technology, Principles and Applications for DNA Amplification (H. A. Erlich, Ed.), pp. 7–16 (1989).)

Some amplification techniques take the approach of amplifying and then detecting target; others detect target and then amplify probe. Regardless of the approach, the sample containing nucleic acid must be free of inhibitors for amplification to occur at high efficiency.

Amplification "reagents" are defined as those reagents (primers, salt, buffers, lables, deoxyribonucleotide triphosphates, etc.) needed for amplification except for nucleic acid and the amplification enzyme. Typically, amplification reagents along with other reaction components are placed and contained in a reaction vessel (test tube, microwell plate, microfuge tube, etc.). Synthetic oligonucleotide primers are available commercially. See Perkin-Elmer Cetus Biotechnology Catalog, Oligos, Etc. and other companies.

If a biological sample is the source of nucleic acid, one may disrupt the cellular integrity of the biological sample by applying a lysate to the sample. One lysing agent is protease K. Protease K is a proteolytic enzyme from *Tritirachium album*. It is particularly useful in the present invention because it has no significant DNase activity and, therefore, does not degrade nucleic acid which would prevent amplification. It is also attractive because it is inexpensive and commercially available (e.g., Sigma, St. Louis, Mo., U.S.A., catalogue No. p4914 "Proteinase K"). Various treatment conditions using protease K have been found useful. It is preferred that a high concentration of protease K (e.g., 1.5–2.5 mg/ml) be used for short (5–10 minutes) incubation periods to completely degrade cellular and viral protein and expose viral nucleic acid for amplification. When lower concentrations of protease K (e.g., 0.5 mg/ml) are used, longer incubation periods (30–60 minutes) are required to achieve the same effect. Other lysis approaches are also contemplated, including lysis by heating.

The present invention also contemplates labeling methods wherein the oligonucleotide primer sequences have at least one label attached or integrated into its structure. One embodiment of the present invention is an adaptamer with a label attached at the 5' end. Labels are generally intended to facilitate the detection of the nucleic acid in subsequent steps. Labels are chosen from the group consisting of enzymes, fluorophores, high-affinity conjugates, chemiphores and radioactive atoms ("radiolabels"). While other labels may be used, the present invention contemplates: 1) the enzymes alkaline phosphatase, beta-galactosidase and glucose oxidase; 2) the affinity conjugate system of biotin-avidin; 3) the fluorophore that is fluorescein; 4) the chemiphore that is luminol; and 5) the preferred radiolabels $^3$H, $^{14}$C and $^{32}$P. Oligonucleotides may be 3' end-labeled with [$\alpha$-$^{35}$S] dATP to specific activities in the range of $1\times10^{10}$ dpm/$\mu$g using terminal deoxynucleotidyl transferase. Unincorporated labeled nucleotides can be removed from the nucleotide probe by centrifugation through a Sephadex G-25 column or by elution from a Waters Sep Pak C-18 column. Where the nucleic acid (primer, adaptamer, target, foreign, first-fourth) is labeled, the labels can include radioisotopes, fluorophores, enzymes, luminescers or particles. These and other labels are well known in the art and are described, for example, in the following U.S. Pat. Nos. 3,766,162; 3,791,932; 3,817,837; 3,996,345; and 4,233,402.

"Detection" of PCR-amplified nucleic acid refers to the process of observing, locating, or quantitating an analytical signal which is inferred to be specifically associated with the product of PCR amplification, as distinguished from PCR reactants. The analytical signal can result from visible or ultraviolet absorbance or fluorescence, chemiluminescence, or the photographic or autoradiographic image of absorbance, fluorescence, chemiluminescence, or ionizing radiation. Detection of in situ PCR products involves microscopic observation or recording of such signals. The signal derives directly or indirectly from a molecular "tag" attached to a PCR primer or dNTP or to a nucleic acid probe, which tag may be a radioactive atom, a chromophore, a fluorophore, a chemiluminescent reagent, an enzyme capable of generating a colored, fluorescent, or chemiluminescent product, or a binding moiety capable of reaction with another molecule or particle which directly carries or catalytically generates the analytical signal. Common binding moieties are biotin, which binds tightly to streptavidin or avidin, digoxigenin, which binds tightly to anti-digoxigenin antibodies, and fluorescein, which binds tightly to anti-fluorescein antibodies. The avidin, streptavidin, and antibodies are easily attached to chromophores, fluorophores, radioactive atoms, and enzymes capable of generating colored, fluorescent, or chemiluminescent signals.

For this purpose, nucleic acid molecules generated by the present invention or their subsequent expression products can be radioactively labeled metabolically in vivo by culturing cells expressing the nucleic acids generated in the presence of $^{35}$S-cysteine and $^{35}$S-methionine (200 Ci/ml) in RPMI 1640 medium devoid of these two amino acids and supplemented with dialyzed fetal calf serum. After 16 hours, the labeled protein may be harvested from the culture supernatant by centrifugation over a 20% sucrose cushion at 100,000 g for 1,5 hours if such protein is secreted from the cell. Otherwise, the cells may be collected and the protein purified. The resulting pelleted protein is then resuspended in RIPA buffer (20 mM triethanolamine, pH 8.0, 0.5M NaCl, 0.5% Nonidet P40, 0.1% sodium deoxycholate, and 1 mM phenylmethylsulfonylfluoride).

"Nucleic acid probe" refers to an oligonucleotide or polynucleotide containing a sequence complementary to part or all of the PCR target sequence, also containing a tag which can be used to locate cells in an in situ PCR preparation which retains the tag after mixing with nucleic acid probe under solvent and temperature conditions which promote probe annealing to specifically amplified nucleic acid.

A probe generated in such a manner can be employed in a diagnostic test for specific detection of a particular nucleic acid which incorporates the following essential steps: (1) labeling of the probe generated as described above by the methods previously described; (2) bringing the probe into contact under stringent hybridization conditions with DNA from, once said DNA or RNA has been, preferably, applied to a membrane and has been rendered accessible to the probe, (3) washing the membrane with a buffer under circumstances in which stringent conditions are maintained, detection of the labeled probe, preferably by autoradiography in cases in which the probe has been radioactively labeled, or by a suitable immunodetection technique in case the probe has been labeled chemically.

RNA is prepared by any number of methods; the choice may depend on the source of the sample and availability. Methods for preparing RNA are described in Davis et al., 1986, Basic Methods in Molecular Biology, Elsevier, New York, Chapter 11; Ausubel et al., 1987, Current Protocols in Molecular Biology, Chapter 4, John Wiley and Sons, New York; Kawasaki and Wang, 1989, PCR Technology, ed. Erlich, Stockton Press New York; Kawasaki, 1990, PCR Protocols: A Guide to Methods and Applications, Innis et al. eds. Academic Press, San Diego; and Wang and Mark, 1990, PCR Protocols: A Guide to Methods and Applications, Innis et al. eds. Academic Press, San Diego; all of which are incorporated herein by reference.

As used herein, "specific hybridization" occurs when a probe hybridizes to a target nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, Ausubel, F., et al., Methods in Enzymology [*Methods in Enzymology* Vol. 152, (1987) Berger, S. and Kimmel, A. ed., Academic Press, New York] or *Hybridization with Nucleic Acid Probes* all of which hereby are incorporated herein by reference.

High stringent hybridization conditions may be selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide comcentration, and the extent of base mismatching, the combination of parameters is more important than the absolute measure of any one. For example high stringency may be attained for example by overnight hybridization at about 68° C. in a 6× SSC solution, washing at room temperature with 6× SSC solution, followed by washing at about 68° C. in a 6× SSC in a 0.6× SSX solution.

Hybridization with moderate stringency may be attained for example by: 1) filter pre-hybridizing and hybridizing with a solution of 3× sodium chloride, sodium citrate (SSC), 50% formamide, 0.1M Tris buffer at Ph 7.5, 5× Denhardt's solution; 2.) pre-hybridization at 37° C. for 4 hours; 3) hybridization at 37° C. with amount of labelled probe equal to 3,000,000 cpm total for 16 hours; 4) wash in 2× SSC and 0.1% SDS solution; 5) wash 4× for 1 minute each at room temperature at 4× at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectivly hybridizing it is meant that a probe binds to a given target in a manner that is detectable in a different manner from non-target sequence under high stringency conditions of hybridization. in a different "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., [Sambrook, et al. (1989) *Molecular Cloning: A Laboratory Manual* (2nd ed.), Cold Spring Harbor Laboratory, Vols. 1–3.] or Ausubel, F., et al., [Ausubel, F., et al. (1987) *Current Protocols in Molecular Biology*, New York.].

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, or by the triester method according to Matteucci, et al., [Matteucci, et al. (1981) *Am. Chem. Soc.* 103:3185.], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

One advantage of the present invention is that it allows one to bypass the requirement of an intermediate host (e.g. *E. coli* and eliminates the need for ligation in library construction. Another advantage of the present invention is that it permits a "prethought" orientation to be constructed by simple altering of the adaptamer "junction" fragment. Whichever sequences are chosen for the 5' and 3' regions of the adaptamers will then dictate the final configuration of the fragment arrangement.

Figure 2:
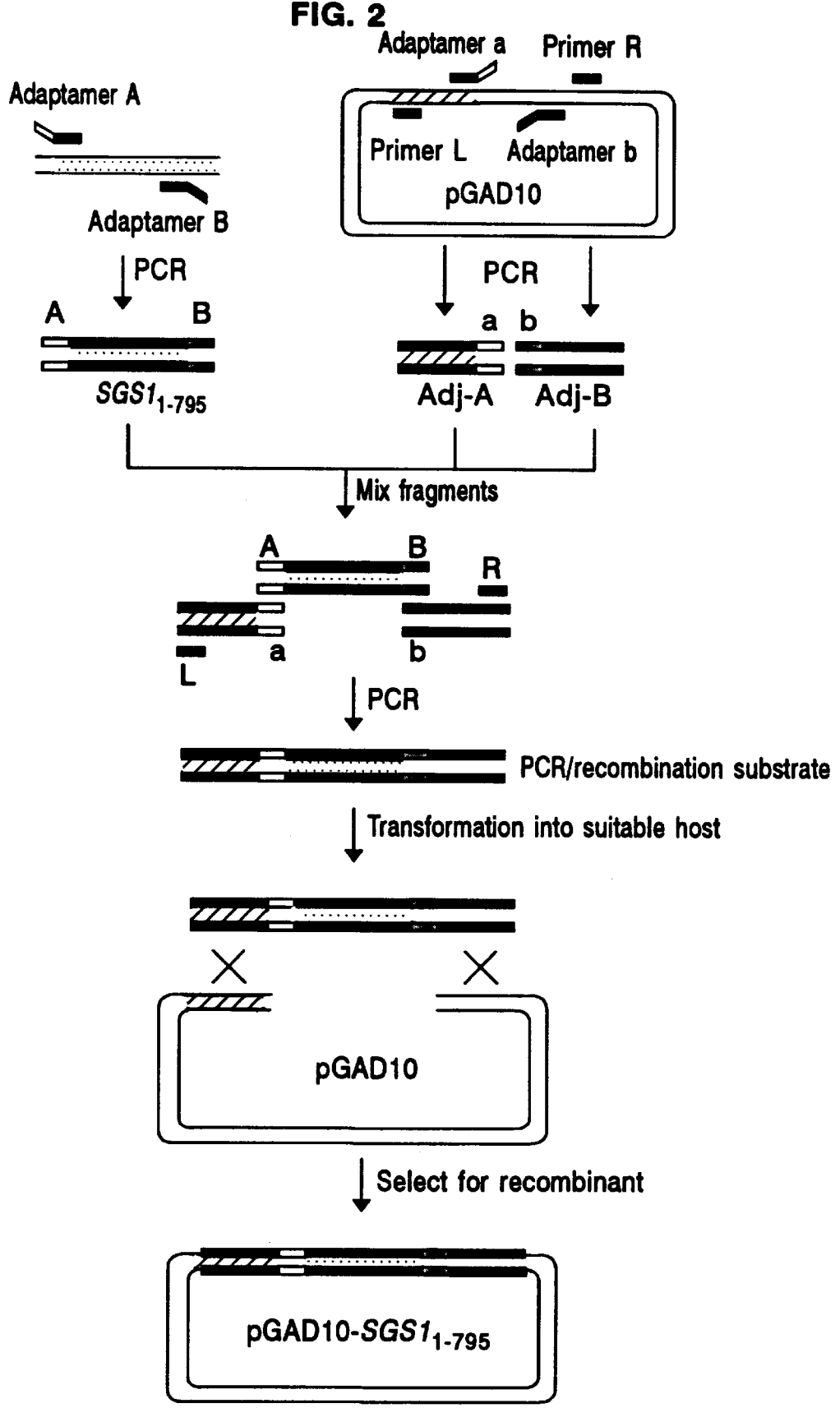

As to FIG. 2, the choice of the fourth molecule, which sequences are amplified from it and which sequences are linked to it in the adaptamer determines what the fusion will be. In the region that is homologous on either molecule [(labeled Adj-A in FIG. 2) or (labelled Adj-B in FIG. 2)], the adaptamer is designed so that the amplified molecule (labeled SGS1 $_{1-795}$ in FIG. 2) fuses in a prearranged, preplanned fashion with the adjacent fragments. This will be the end product of the second round of PCR.

The present invention provides for adaptamers (an adapted type of primers) that use the common sequences that flank every member of the library. One or both of the adaptamers may contain additional designed nucleotides (1 nucleotide, 2 nucleotides or n nucleotides) inserted between the complementarity of the adaptamer used on the EST molecule. (See FIG. 6). A specific example may be using 0, 1 and 2 would produce one in three in-frame fusions from randomly ended (i.e. in the middle of coding sequence) ORF (open reading frame) sequences. When n is larger, any pre-arranged sequence that can be synthesized via synthetic oligonucleotide chemistry can be inserted at a precise point for all of the memebers of a library. These extra nucleotides could be DNA binding sites or tags or they could encode "extra" amino acids that might give flexability to the novel joint created between the sequences or the extra nucleotides might give rise to or provide an antigen or other kind of protein tag.

The present invention provides for a method like the method recited on page 9 hereinabove, wherein the 3' end of the primer described in 1 (A) (i) (a) is homologous to a common replicative element (e.g. Alu sequence, LINE, B1, etc.). In this case, the orientation of the other primer must be toward the 5' direction of the ORF. This permits promoter capture.

Linking two fragments is the minimum for adapting any random sequence by PCR/recombination-directed library construction. See FIGS. 12, 13 and 14A–F. Any number of fragments may be linked together. All that is required is that the adaptamers at each end are unique and will not overlap any other adaptamer (except the correct complementary one) or amplify any internal sequences (because this could cause incorrect joints or connections between fragments to be formed). This permits the fusion of novel sequences adjacent to any other fragment.

Figure 16:
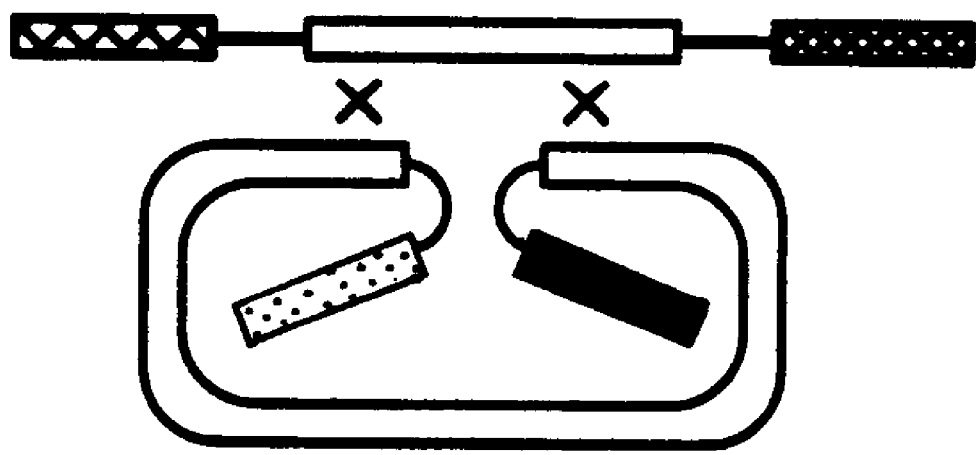

The present invention also provides for circular molecules. A circular molecule may be formed in some organisms (such as mammalian cells) if one can counterselect a genetic marker that is placed on the ends of the preliminary linear molecule (the starting material). Such a scheme would require an additional fragment to be added to the ends of each circular molecule which could be done by using adaptamers as described herein. FIG. 16 shows the configuration of this recombination event in an extreme version—all four ends have counterselectable markers.

In the practice of the present invention, specific sequence requirements of each particular use must be known in order to prevent adaptamers from priming non-productive products, that is products which would not work as starting material for the next step of the method. The sequences chosen for amplifying two different fragments from the second molecule must be very carefully defined. FIG. 14A illustrates an insertion and FIG. 14B illustrates an insertion accompanied by a deletion if Adaptamer b and Adaptamer A are separated thus having some distance of sequence between them. FIG. 14C depicts an insertion accompanied by a duplication which may be obtained if the sequences projected for amplification from each pair of primers (Primer L/Adaptamer A and Adaptamer b/Primer R) cross one another upon amplification. The figure shows what will happen after the PCR/recombination fragment is synthesized and is introduced back into the parental molecule (ii) which was used to generate the flanking sequences that allowed recombination.

The configuration shown in FIG. 14D is also important in that it can be used to "gap repair" a genomic sequence that lies between the position of adaptamers (c) and (f) This is not directly related to library construction, but it is a useful kind of manipulation that is possible with adaptamers. Similarly, the FIG. 14E configuration may be used for directed gene replacement on a per gene basis and is not useful for library construction. It is useful in the following situations: A mutation from one strain of yeast can be transferred into another strain of yeast by designing the c, d, e, and f adaptamers as shown in FIG. 14C making sure that the mutation of interest is in the shaded (and thus duplicated) region. As this PCR/recombination fragment is introduced into the genome of interest (one without the mutation), recombination removed the non-mutated region and replaces it with an insertion flanked by a duplicated copy of the mutated region. A second recombination event, this time direct repeat recombination, can be selected resulting in the loss of the intervening insertion and leaving a single copy of the mutated sequence in the genome. A variation of this method has been carried out in yeast and would probably work in mammalian cells as well. This invention provides for genetic manipulation of genomes using PCR/recombination-directed methods.

The present invention provides a method for the use of adaptamers to create two separate molecules for recombination into the genome such that the host organism resolves them into the correct configuration. The present invention provides for a combination of fusion of two nucleic acids and the reiteration of such method of generating a fused nucleic acid molecule so as to fuse two or more nucleic acid molecules. FIG. 14D shows the pairing required for this integration. In this embodiment, the adaptamers for the two fragments are designed to yield an overlap for the selectable marker such that only recombination in the appropriate alignment will result in a functional gene. The present invention provides for the addition of "blocking" counter-selectable markers at the two ends that pair with the target DNA.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

One embodiment of the subject invention is to optimize the steps necessary to utilize a newly developed technique called PCR/recombination-directed library construction to facilitate genome-wide analysis. The method may utilize the "EST" sequences deposited in dbEST. At least four separate embodiments may be enumerated:

(i) Optimization of the use of unique primers called "adaptamers" (see FIGS. 1 and 2) to construct libraries directly in yeast avoiding completely the need to use bacteria as an intermediary.

(ii) Augmentmentation of high frequency transformation methods so that they can be scaled up for the efficient introduction of these libraries into the appropriate host cells.

(iii) Design of adaptamers to permit the amplification of random EST clones and their in-frame fusion with DNA binding domains and transcriptional activation domains for use in the two-hybrid system.

(iv) Optimization of the construction of two-hybrid fusion proteins using adaptamers and mRNA (cDNA) as the template to obviate the necessity of having a full length clone in hand to make a fusion for two-hybrid analysis.

The methods outlined here are not specific for mammalian sequences and can be applied to any sequenced genome. For example, a two-hybrid library for any sequenced genome (e.g., bacteria) can be constructed in yeast using adaptamers.

The availability of the complete genomic sequences for several organisms as well as extensive EST databases for several others provides a challenge and an opportunity to exploit this information creatively to help determine the function of these genes. By applying genome-wide experimental approaches, one can both facilitate and further the study of biology in these systems with great power. For example, construction of an arrayed library of genes/ESTs for use in a two-hybrid analysis is a logical next step for the characterization of these open reading frames. One approach to constructing such libraries involves the creation of random libraries, first by cloning cDNAs into vectors, tranforming bacteria and then transferring the clones into yeast. The experiments are performed such that only information about positive interactions can be derived. Given that there is now considerable data being collected for many potential ORFs, such as ESTs or ORFs from complete genomic sequences, a more direct method of library construction is possible that bypasses the need to create random clone libraries. Instead, clones can be made from the sequence information by creating a PCR-generated fragment that is designed to contain overlapping sequence with the target vector. Co-transformation of this PCR fragment and the linearized vector directly into yeast selects for efficient in vivo recombinants. In addition, as the primers are designed from known sequences, in the cases where sequences at the 5' and 3' ends of an open reading frame are known, the clone can be generated directly from mRNA without the need for a full length cDNA clone.

Methods to simplify the construction of an arrayed library may be carried out by combining PCR methods and the power of homologous genetic recombination ("PCR/recombination-directed library construction"). The system described is an "open" system: once created, any type of gene fusion can be made in a completely specific, arrayed, genome-wide library.

The development of these libraries and demonstration of the feasibility of this approach may provide the basis for the construction of genome-wide libraries. The distribution of such libraries within the research community will provide powerful and flexible tools for all biologists who will be exploring the function of genes. These approaches may also provide a paradigm for studies in other systems that may take place in the future.

Preliminary Studies

There are established methods and methods in development regarding the manipulation of yeast. These include gene targeting [1] and gene disruptions methods [2] that utilize genetic recombination for genome alterations.

Several yeast strains have been developed to produce a mating method for streamlining two-hybrid analysis [3]. Recently, a cycloheximide resistance marker, cyh2, has been introduced into these strains to permit the rapid counter-selection of a plasmid bearing a CYH2 wild type gene. The strains already have can1 mutations to permit the counter-selection of a plasmid-borne CAN1 gene. The combination of these counterselectable markers into two-hybrid plasmids is used to help screen out false positives.

There exists experience with PCR methodology of one of skill in the art to include the design and successful implementation of 376 STSs for human chromosome 13 [4]. PCR has been used to generate long fragments of the mouse Rad52 genomic sequence to determine the primary sequence of more than 21 kb of this gene. 2 to 3 kb PCR products are routinely generated which can be directly used on an ABI sequencer.

It has been established that yeast cells will efficiently recombine overlapping fragments to create circular molecules. As few as 20 nucleotides of homology can be used as the recombination substrates however, the efficiency is low and there is the possibility that aberrant events can be generated [5, 6]. To obviate the necessity to synthesize longer oligomers to increase the efficiency of the recombination event, an approach has been designed that extends the overlapping homology using PCR in a generic fashion so that only a single set of unique primers need to be constructed for each fragment of interest. These primers have been termed adapted primers or "adaptamers."

To demonstrate the feasibility of the adaptamer approach to create clones, the following experiment was performed. As shown in FIG. 1, an adaptamer is a PCR primer that contains additional DNA sequence on its 5' end (a tag, an adapted region) to permit fusion to any adjacent sequence containing the complementary sequence to the tag. For open reading frames, the convention was adopted that the 5' end adaptamer is called A and the 3' end adaptamer, B. A lower case letter (a or b) is used to indicate a complementary adaptamer. The fragments used as recombination substrates are named Adjacent-A (Adj-A) and Adjacent-B (Adj-B) and are made from adaptamer a and primer L and adaptamer b and primer R (see FIG. 2 for orientations) that are homologous to the target vector. The length of Adj-A and Adj-B determine the amount of overlap with the target vector.

In the test experiments of this strategy, two 36 nucleotide long adaptamers were designed. Adaptamer A contains 18 nucleotides of homology at the AUG start codon of the SGS1 open reading frame [7] and adaptamer B, 18 nucleotides of homology ending at codon 795. The 18 nucleotides comprising the A and B tag sequences overlap with the insertion site on the pGAD10 vector used for two-hybrid analysis [8]. Adaptamer a and primer L generate a 255 bp product on one side of the cloning site of pGAD10 while adaptamer b and primer R generate a 250 bp fragment from the other side of the cloning site. The A/a and B/b sequences were designed so that the 795 aa ORF of Sgs1 would be fused in frame with the activation domain of pGAD10. This creates a fusion protein that can interact with Top3, which has been fused to the Gal4 DNA binding domain. These constructs were used so that one could validate the in vitro PCR and recombination reactions since successful clones will turn blue when yeast transformants are mated to the Top3 fusion strain. In addition, the adaptamers were designed so that the untemplated A often added by the Taq polymerase would not disturb subsequent pairing and priming reactions.

Figure 3:
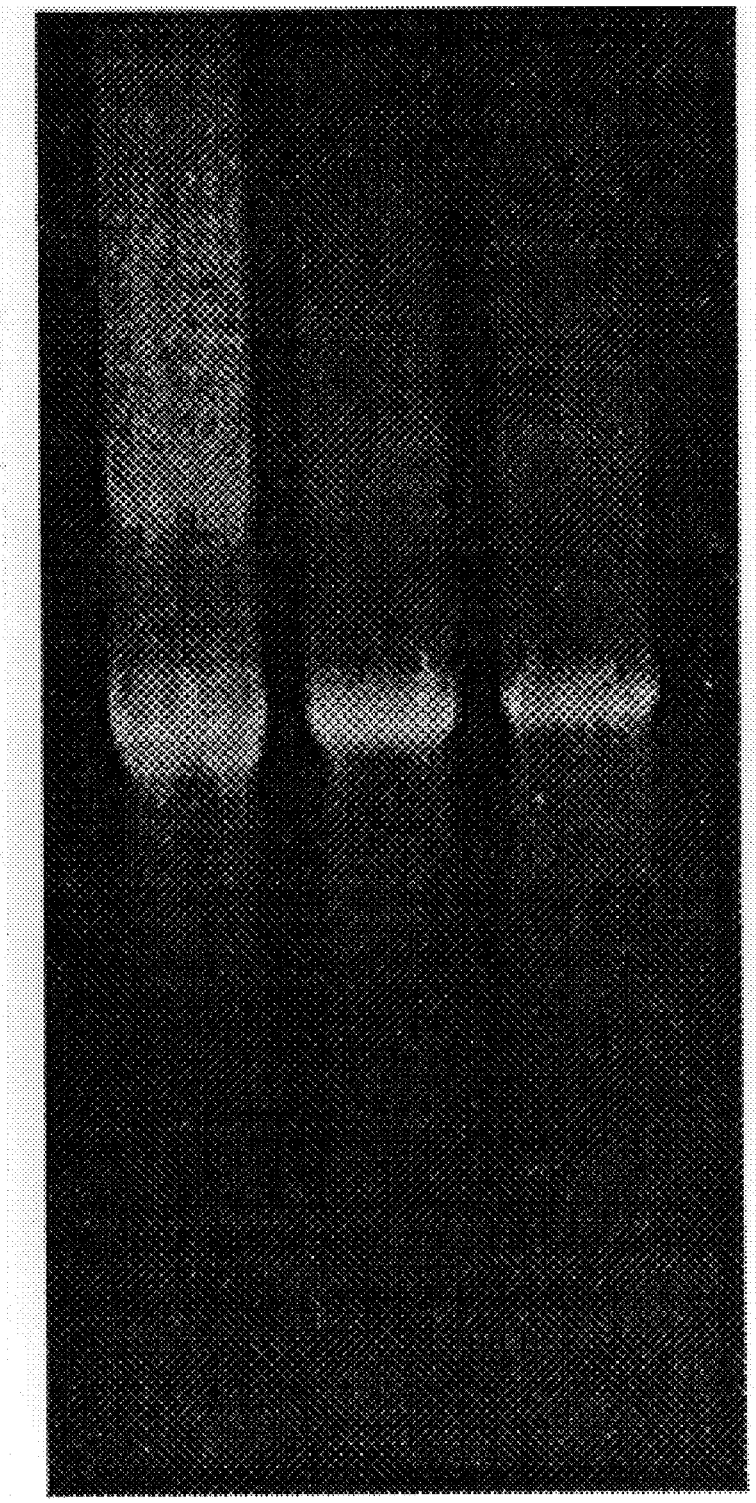

Two experiments were performed with these primers. First, the three PCR products were generated using 30 cycles at standard PCR conditions (94° C., 30"; 55° C., 15"; 73° C., 30") and gel purified. They were mixed in two different ratios (Adj-A:Sgs1:Adj-B): 1:2:1 and 1:4:1 and excess primers L and R (1 $\mu$M) were added and "long" PCR was performed (94° C., 10"; 55° C., 30"; 72° C., 4' for 10 cycles then 20 cycles where the 72° C. step is ramped by extending each cycle 30 additional seconds). Both gave the same result which is illustrated in FIG. 3 as a clean, 2.8 kb fragment (FIG. 3, lanes 2 & 3). At the same time, the three fragments were mixed at equimolar concentrations prior to gel purification of the PCR products and similar results were obtained (FIG. 3, lane 1). The products of these PCR reactions were used directly in a co-transformation experiment with linearized pGAD10 that was digested with XhoI and EcoRI to help reduce background religation events of the vector.

Yeast transformation by both electroporation and lithium acetate methods was performed. For electroporation, co-transformation with 100 ng of vector and 100 ng of the PCR/recombination substrate resulted in 564 transformants, 15 times more than the 35 observed with vector alone. For lithium, it was found that more than 8,000 transformants occurred when the two fragments were co-transformed as compared to 200 for the vector alone. A sample of the transformants were tested for fidelity by measuring their ability to form blue colonies after mating with a strain bearing the TOP3-GDB fusion. 95% of the colonies turned blue.

Figure 4:

In addition, FIG. 4 shows 15 out of 16 transformants from a similar experiment exhibit the correct recombination joints. These results indicate that PCR/recombination-directed library construction would work and is a feasible method.

It was also demonstrated that mRNA may be used directly in a PCR/recombination-directed cloning experiment. The use of mRNA directly, obviates the need to have a full-length copy of the cloned gene of interest. Additionally, any fragment of a gene can be cloned into a vector of choice just by choosing the appropriate sequences for the adaptamers. In the test described herein, adaptamers were made to the mouse RAD52 gene starting at amino acid 56 and ending 370 bases from the termination codon (a 1366 nucleotide long fragment). 20 $\mu$g of total mouse RNA from 7.5 day mouse embryonic liver was converted to DNA in a 33.5 $\mu$l reaction using 2.5 $\mu$M oligo d(T)$_{16}$ (Perkin-Elmer, Cat. No. N808-128) as a primer. The reaction was heated to 65° C. for 15 minutes and 60 units of mRNazin (Promega, Cat. No. N251A), 1 nM each of dATP, dCTP, dGTP and dTTP. 0.1 $\mu$g/ml final BSA and 100 units of M-MuLV reverse transcriptase (NE BioLabs, Cat. No. 253L) were added in RT buffer (NE BioLabs). After 1 hr at 37° C., the 50 $\mu$l reaction was extracted twice with phenol:chloroform, ethanol precipitated and resuspended in 50 $\mu$l of H$_2$O. 3 $\mu$l of the cDNA was used for two "long" PCRs (94° C., 10"; 55° C., 30"; 72° C., 4' for 10 cycles then 20 cycles where the 72° C. step is ramped by extending each cycle 30 additional seconds). The reaction products were gel purified ($\approx$10 ng total) and resuspended in 20 $\mu$l. 1 $\mu$l of this was used for a second round of "long" PCR and again gel purified. Adj-A and Adj-B (described above) were mixed in three different molar ratios (Adj-A:Rad52:Adj-B): 15:1:29; 2:1:4 and 3:1:2 and excess primers L and R (1 $\mu$M) were added. In addition to the expoected 1.9 kb fragment, the 15:1:29 ratio gave a smaller and more intense band. This reaction was not used for further experiments. The 2:1:4 and 3:1:2 ratio reactions each gave the expected 1.9 kb fragment. These fragments were gel purified and used in a co-transformation experiment with linearized XhoI-EcoRI-digested pGAD10. Table 1 below shows the results.

| Ratio | PCR/recombination fragment | pGAD10 vector | Number of transformants | Number of insert positive clones |
|---|---|---|---|---|
| 2:1:4 | 0 | 12 ng | 160 | not applicable |
|  | 1.25 ng | 12 ng | 2,040 | 5/55 |
|  | 5 ng | 12 ng | 4,540 |  |
| 3:1:2 | 0 | 12 ng | 39 | not applicable |
|  | 18 ng* | 12 ng | 1056 | 1/22 |
|  | 12 ng | 12 ng | 156 | 12/18 |

*this sample was not gel purified before transformation

Among the insert positive clones, some clones were found that were approximately 100 nucleotides shorter that the expected size shown in FIGS. 17A–17B (compare lanes 4 and 5 of FIG. 17B). DNA sequence analysis of one of those clones revealed that it arose from a PCR product representing alternatively spliced mRNA similar to what has been observed that such sized fragments are produced from cloned cDNAs.

Research Design and Methods: Optimization of PCR/recombination-directed library construction As described in the hereinabove in the preliminary results section, it has been demonstrated that PCR/recombination-directed library construction is a viable approach for making clones. However, the optimization of several steps are necessary before this method can be applied to genomic scale. The length of the adjacent fragments in the first experiments were approximately 250 nucleotides. At this length, over 95% of the recombinant clones were correct.

Optimization of this length is important since the shorter these sequences are, the less they contribute to the overall length of the PCR product that recombines with the vector. At the same time, it is essential not to shorten these sequences too much as to reduce the efficiency of recombination in yeast. For all of the experiments described in this section, the same $SGS1_{1-795}$ fragment described earlier will be used which allows a biological as well as a physical assay for successful constructs (see Preliminary Studies). To optimize the length, the size of Adj-A and Adj-B will be varied from 40 to 500 nucleotides. One may plot not only the efficiency of transformation vs. length but also the percentage correct configurations vs. length. It is expected that 150 to 250 nucleotides will be optimal. However, it may be that 40 or 50 nucleotides are as efficient, thus one could eliminate the second round of PCR necessary to add the extra nucleotides of the adjacent sequences. From the results described herein, it is unlikely that 40 or 50 nucleotides will be optimal.

To optimize the conditions for adding Adj-A and Adj-B, the amount of each product added will be varied, along with the concentration of primers L and R. There are at least two possible scenarios for the addition of these adjacent fragments. In the initial experiments, small amounts of Adj-A and Adj-B and excess primers L and R were added (see Preliminary Studies). It may be possible to eliminate the addition of primers L and R by adding excess Adj-A and Adj-B. These can easily be synthesized as they are always the same for each vector being used.

These manipulations may eventually be performed by a robotics system, thus it is advantageous to remove as many steps as possible and to tailor reaction volumes accordingly. For example, the first PCR reaction to create the gene of interest using adaptamers A and B will be done in the absence of the Adjacent-A and Adjacent-B adaptamers. A small portion (1/100th) will be removed and reacted with the Adj-A and Adj-B fragments to generate the optimally long recombination fragment for co-transformation into yeast with the vector of choice. However, it may be possible to add all of the components to the initial tube and let the PCR generate, in one reaction, the recombination fragment.

(2) Augmentation of high frequency transformation methods.

Besides optimizing the generation of recombination fragments, optimal transformation methods must be developed so that the library is minimally manipulated. Since the two-hybrid system is scored positively only if an interaction takes place, and the clones are made by mating, it is not necessary to have a 100% pure colony to assay. For example, as long as some proportion of the colony contains cells with the appropriate construct, a positive signal will be scored. Therefore, the transformation method must be efficient and easy to scale. It is clear that the $Li^+$ ion method [Ito, et al. J. Bacteriol. 1983, 153:163–68 and Gietz et al. 1992, Nucl. Acids Res. 20:1425] is the easiest to scale. Protocols for 96-well micotitre dish transformations have been developed and are well known to one of skill in the art. One could transpose the volumes and procedures of these methods with respect to the volumes of the PCR used to create the recombination fragment and the vector in order to generate some number of transformants per well. This number can be determined experimentally (30–50 is one possible approximation). Thus, even if cloning artifacts occur during PCR/recombination library construction either by accident or by design (see the next section for the "by design" example), some number of transformants will be correct. Experimentally, one may vary the proportion of positive clones in a colony to determine the percentage required to be correct and still give rise to a positive signal.

The present invention provides for a method that will allow yeast transformtion to take place entirely within the well of a microtiter dish. For such a protocol to be successful, one must ensure high enough efficiency transformation as well as efficient transfer of the mixed transformants to subsequent steps of the procedure. In addtion, the optimization of transformation will take into account the volumes generated by PCR to create. This will be critical for the robotization of the process. However, even if larger volumes are necessary than can easily be accommodated in a microtiter well, one can still miniaturize the process to do multiple transformations at once. Such approaches avoid the purification of the clones which is a time consuming step. In addition, as discussed above, there is a distinct advantage to not purifying clones since positives will arise even if they are only a fraction of the colony.

(3) Design and optimization of random EST cloning.

The adaptamer approach outlined in the introduction can be used to make a clone for any known set of sequences by individually synthesizing a specific set of adaptamers. The use of this approach for the creation of fusions directly from known mRNA sequences will be described in the next section. However, the approach can also be used to create a library from EST sequences that have already been cloned. For example, I.M.A.G.E. has provided Washington University in St. Louis with many EST libraries. Many of these clones have been sequenced and they comprise dbEST. Sequences from these ESTs can be inserted directly into two-hybrid fusion vectors using the strategy described below. Two assumptions for this strategy are: (1) the 5' ends of the EST clones are often in the coding sequence of the EST, which will permit a productive fusion and (2) most clones do not exceed 5 kb in length as such sequences are not efficiently amplified by PCR.

Figure 6:
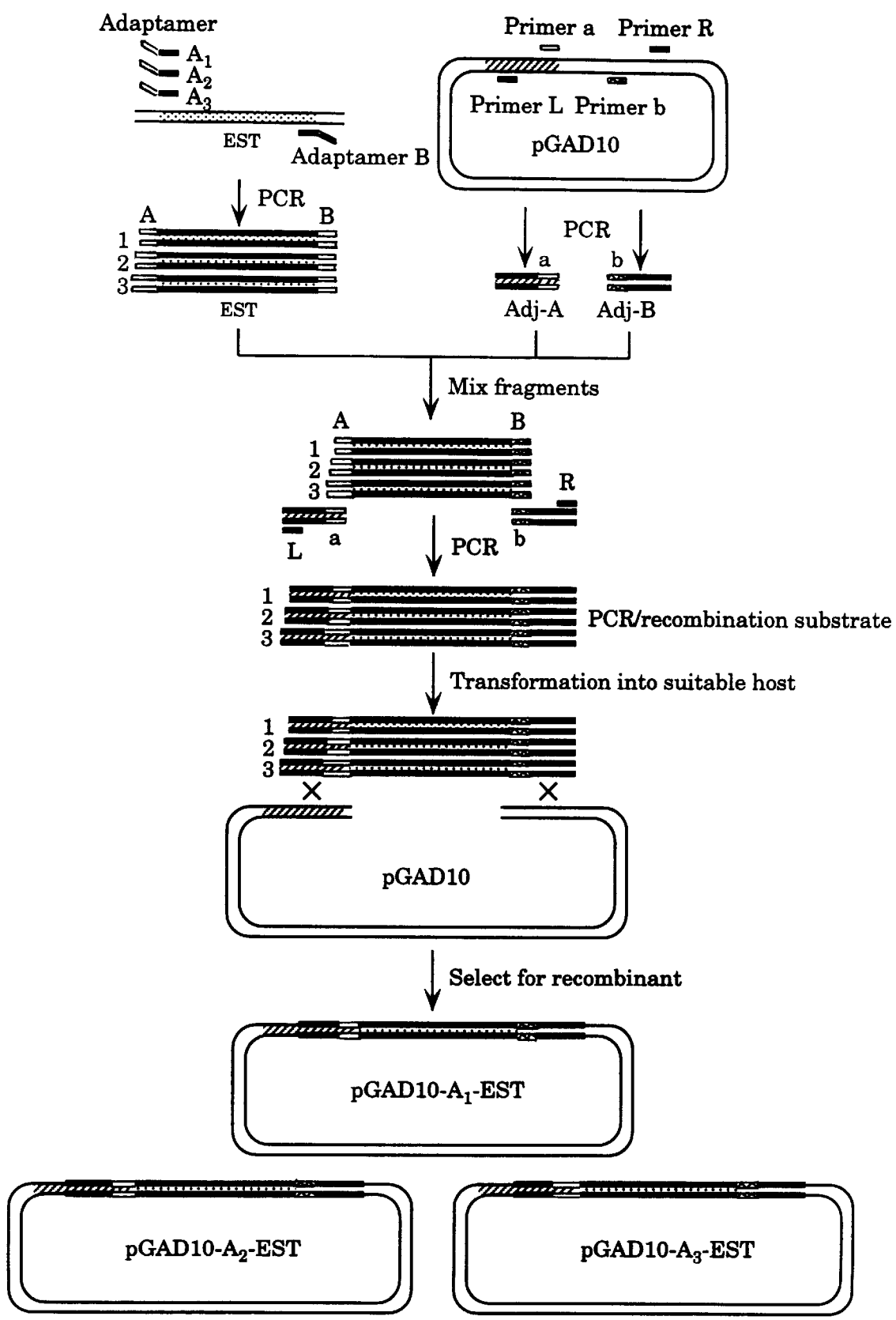

The adaptamers shown in FIG. 5 have been designed to adapt sequences from the I.M.A.G.E. libraries that have been cloned into the pT7T3-D vector. As described in the brief description of FIG. 5, homology to the sequences adjacent to every clone has been built into each adaptamer. In addition, three sets of adaptamers for the 5' ends have been designed to permit fusion to the 5' end of the ESTs. Using this set of adaptamers for each member of one of these libraries will lead to three different DNA sequence fusions of the EST sequence with the DNA sequence of the Gal4 activation domain of plasmid, pGAD10. One in three of these fusions will be in the correct reading frame resulting in a protein fusion of the EST with the activation domain. The scheme for this is shown in FIG. 6.

The products created from the transformation will be a mixture of all three fusions, one of which will be in-frame with the Gal4 activation domain. As discussed in the previous section, only positive interactions are scored, therefore, the out-of-frame fusions will not disturb a potential positive signal unless the positive clone is under-represented in the mixture. A priori the cloning scheme itself does not present any reason for under-representation of any one sequence.

This entire scheme may be tested and analyzed in two ways. Firstly, a set of adaptamers may be created that will recapitulate the three reading frames using the $Sgs1_{1-795}$ fragment described in the preliminary results section. Twenty separate reactions will be tested. The system will be optimized when 95% of the reactions are positive after all of the steps. The second test will be the PCR/recombination cloning of five ESTs from dbEST. EST representatives that have known two-hybrid interactions may be used. In addition one may amplify the five test ESTs with adaptamer B and adaptamers $A_1$, $A_2$ and $A_3$ separately and pick two clones from each reaction. Thus, a duplicate set of 15 different clones will in effect be created. The efficiency of transformation for adaptamers $A_1$, $A_2$ and $A_3$ should be approximately the same and will be a measure of amplification. In addition, the junction sequences from the 30 clones will be determined by DNA sequence analysis. It is expected that each EST fusion will be as predicted. From these experiments and the experiments described in the previous section on the proportion of correct clones necessary to give a positive, it is clear that the feasibility of this general approach for cloning ORFs from ESTs is a step forward from that of the presently used methods of library construction.

(4) Optimization of cDNA cloning.

It has already been shown that adaptamers can be designed to permit the cloning of a known mRNA (see preliminary results). However, the efficiency of cloning directly from mRNA was low. In addition to the optimization of this process, there are several questions that must be addressed before this can be used as a general method for constructing clones directly from mRNA. Firstly, how much background noise or signal is there in using all of the transcribed sequences from an organism? Secondly, how much of problem a are partially spliced messages?

To optimize the procedure, one can use three different messages: mouse Rad52, a low abundance mRNA, mouse GAPDH, a moderate abundance mRNA and mouse actin, a high abundance mRNA. One may also use the yeast two-hybrid interaction system. The adaptamers may be designed for each gene to permit cloning into pGAD10. For mouse Rad52, a successful cloning event would result in a fusion protein that can interact with itself fused to the DNA binding domain (pDBD-Rad52 Mm). The first step in the cDNA cloning is reverse transcription. One can simply evaluate this step by standard gel electrophoresis. Next, adaptamers A and B, specific for each gene will be used to synthesize the three genes from the cDNA. This step will also be evaluated via electrophoresis. At this point, the fragments can be gel purified or used directly with Adj-A and Adj-B and primers L and R to generate the recombination fragment. For each mRNA, it would be possible to recover 50 transformants and analyze them by PCR across the insert site of the vector. This step would determine the percentage of transformants with inserts and will assay for size. For Rad52 Mm, a map exists of many partially spliced mRNAs. Fragments will be amplified from the different size classes that are observed for DNA sequencing to determine what kind of clone the each size class represents.

Analysis of this small number of genes in great detail will provide the kind of data needed to determine how to proceed. For example, if it is found that only one of the genes gives many different inserts, one would be encouraged to expand the sample to include 20 more genes. One would proceed by analyzing these next 20 genes in great detail to be able to generalize on the kind of results that would be expected. On the other hand, if it is found that two or all three of the original genes give many sized inserts, one would use methods to detect the correct constructs. This may include adding an epitope tag to the C terminus of the amplified cDNA using the 3' adaptamer-B. Addition of such a tag will aid in the identification of full length, intact clones.

Finally, mRNA cloning efforts may be compared with clones from dbEST. For example, of ten 5' and 3' sequences of an EST are greater than 1000 bp apart. Specific adaptamers will be designed for several of these genes and compared with the efficiency of cloning the gene from newly synthesized cDNA versus from DNA of the pooled cDNA library from which it was isolated. This will aid in the determination of which is the better approach to creating a clone for any specific gene. The ability to use cDNAs will greatly enhance the versatility of this technology and permit it to be expanded to organisms like *C. elegans* and *D. melanogaster*, whose genomic sequences are becoming known. Thus interesting guesses and estimations can be made about potential genes and these can be fused directly into two-hybrid vectors via the adaptamers and mRNA cloning described.

Example 2

Use of PCR/recombination-directed library construction to create libraries that will facilitate genome-wide analysis of yeast.

This example may be divided into three specific areas of experiments:

(i) A set of unique primers (termed "adaptamers" in this application—see FIG. 1) to every intergenic region on chromosome V will be designed to permit many possible gene fusion, gene disruption and gene insertion strategies. Each adaptamer will have a tag that will allow the fusion of any adjacent sequence by PCR. Using various combinations of adaptamers, two arrayed libraries will be construced.

(ii) The first library will contain the fusion of promoters from every ORF on chromosome V to green fluorescent protein (GFP) gene cloned into a circular autonomously replicating plasmid. Introduction of this library into various strains will permit a "readout" of gene expression for each promoter under different conditions (e.g., various carbon sources, differing osmolarity, after irradiation, etc.) or in different genetic backgrounds (e.g., various deletions such as transcription factors, rad genes, etc.). The library will be transferred from strain to strain by using a karl mutation that blocks nuclear fusion but permits the transfer of plasmids or chromosomes between nuclei.

(iii) The second library will contain a gene disruption of each chromosome V ORF in a vector specifically designed to permit the liberation of the disrupting fragment after transfer into the strain of choice. Once again, a karl mutant strain will be used as the host strain. In addition, unique restriction sites (I-SceI) and an inducible copy of the I-SceI enzyme will be included in this plasmid. Upon transfer into the recipient nucleus, the I-SceI enzyme will be induced, releasing the disruption fragment and thereby stimulating its integration into the recipient genome.

Background and Significance

The availability of the complete genomic sequences for several organisms provides a challenge and an opportunity to exploit this information creatively. Genome-wide experimental approaches can both facilitate and further the study of biology in these systems with great power. Yeast, being the first sequence-complete eukaryotic organism, combined with its ease of genetic manipulation, offers an ideal system for the development of technologies to explore genome-wide approaches. For example, gene disruptions of every open reading frame in yeast is now possible. However, most strategies invariably construct "static" libraries in a particularly chosen yeast strain. Although valuable, there is a loss of versatility in that the particular needs would not be met for many researchers who would like to introduce a disruption set into a strain(s) containing their unique assay. The next generation of systems to overcome this limitation is described herein. The design of and construction of libraries that can be ported to any strain simply by mating is described. In conjunction with this, methods are described to simplify the construction of an arrayed library using PCR methods and the power of homologous genetic recombination ("PCR/recombination-directed library construction"). The system described is an "open" system: once created, any type of gene fusion can be made in a completely specific, arrayed, genome-wide library. To demonstrate the feasibility of such an approach, disruption of all of the open reading frames on one yeast chromosome may be carried out. Specifically:

(i) A set of unique adaptamers to every intergenic region on chromosome V will be designed to permit many possible gene fusions, gene disruptions and gene insertion strategies. Each adaptamer will have a tag that will allow the fusion of any adjacent sequence by PCR. Using various combinations of adaptamers, two arrayed libraries will be constructed.

(ii) The first library will contain the fusion of promoters from every ORF on chromosome V to green fluorescent protein (GFP) gene cloned into a circular autonomously replicating plasmid. The library will be portable by using a strain containing a kar1 mutation to block nuclear fusion but permit the transfer of plasmids between nuclei. The transfer of this library into various strains will permit a "readout" of gene expression for each promoter under different conditions (e.g., various carbon sources, differing osmolarity, after irradiation, etc.) or in different genetic backgrounds (e.g., various deletions or specific mutations in transcription factors, rad genes, etc.). This will facilitate identification of genes whose regulation changes in response to various conditions or loss of "your favorite gene."

(iii) The second library will contain a gene disruption of each chromosome V ORF in a vector specifically designed to permit the release of the disrupting fragment after transfer into the strain of choice. Once again, a kar1 mutant strain will be used as the host. In addition, unique restriction sites (I-SceI) and an inducible copy of the I-SceI enzyme will be included in this plasmid. Upon transfer into the recipient nucleus, the I-SceI enzyme will be induced, liberating the disruption fragment and thereby stimulating its integration into the recipient genome.

The development of these libraries and demonstration of the feasibility of this approach will lead to the construction of genome-wide libraries. The distribution of such libraries within the research community will provide powerful and flexible tools for all biologists who will be exploring the function of genes. These approaches will also provide a paradigm for studies in other systems that will take place in the future.

Research Design and Methods (1) Adaptamer design for intergenic regions.

FIG. 1 illustrates a typical genomic region from yeast. Adaptamers A and B are oriented on each gene's 5' and 3' ends, respectively. The following design for intergenic adaptamers is set forth: irrespective of gene orientation, each intergenic region is alternately flanked by adaptamer pair C and D followed by adaptamer pair E and F. This design insures that the intergenic regions flanking every gene can be correctly oriented during the PCR fusion steps. C, D, E and F will be random sequences that are not found in yeast and do not contain any start codons to avoid premature translation initiation when promoter fusions are made. The priming sequence for the adaptamers will be selected so that the PCR reaction will amplify the entire intergenic region. However, when an intergenic region is large (>1 kb), a second set of adaptamers will be synthesized (shown in FIG. 1 as E' and F' between FUS1 and YCL26C). In such a case, E and F' are used for FUS1 and E' and F for YCL26C manipulations.

(2) A promoter fusion library.

Using exactly the same approach as outlined in the preliminary studies section hereinabove, a promoter fusion library may be created for all of the genes on chromosome V. Adaptamers for every open reading frame on chromosome V may be synthesized. Each promoter sequence may be PCR-fused with GFP [9] as the reporter gene. This reporter is easy to assay and does not require any sophisticated equipment. Since one goal and embodiment of this application is to make this library easily portable, many labs will be able to utilize the fusions in their favorite strain or mutant background.

Figure 7:
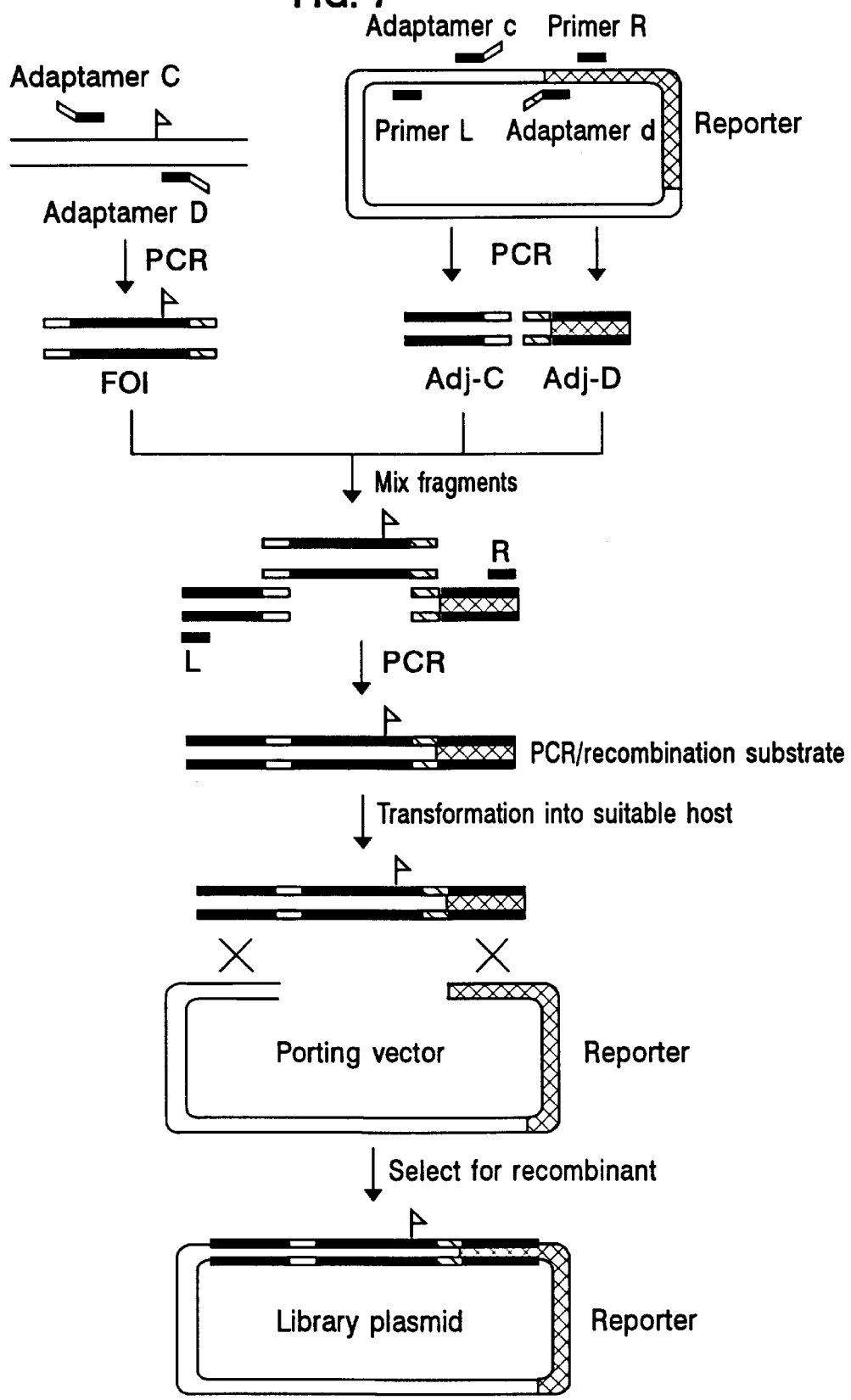

FIG. 7 outlines the basic steps for making the promoter fusion library using PCR/recombination. In the figure, only the synthesis of Adj-C and -D is shown, which is only one of four different combinations (Adj-D and -C; Adj-E and -F; Adj-F and -E are the others). Thus, depending on the orientation of the specific promoter, different adaptamers would be used with primers L and R. The synthesis of all of the Adj's will be made in a large batch and used for all of the constructs in the appropriate orientation. PCR amplification may be combined with PCR of the fragment of interest (FOI) with the PCR fusion to pairs of Adj's in one reaction.

Finally, it may be verified that the PCR and subsequent transformation into yeast did not introduce mutations into the GFP reporter gene. For each construct, an amplification of the GFP ORF with one of the primers containing a T7 promoter will be carried out. This fragment will be transcribed and translated in vitro and assayed for fluorescence.

(3) Construction of the kar1 donor strain.

Figure 8:
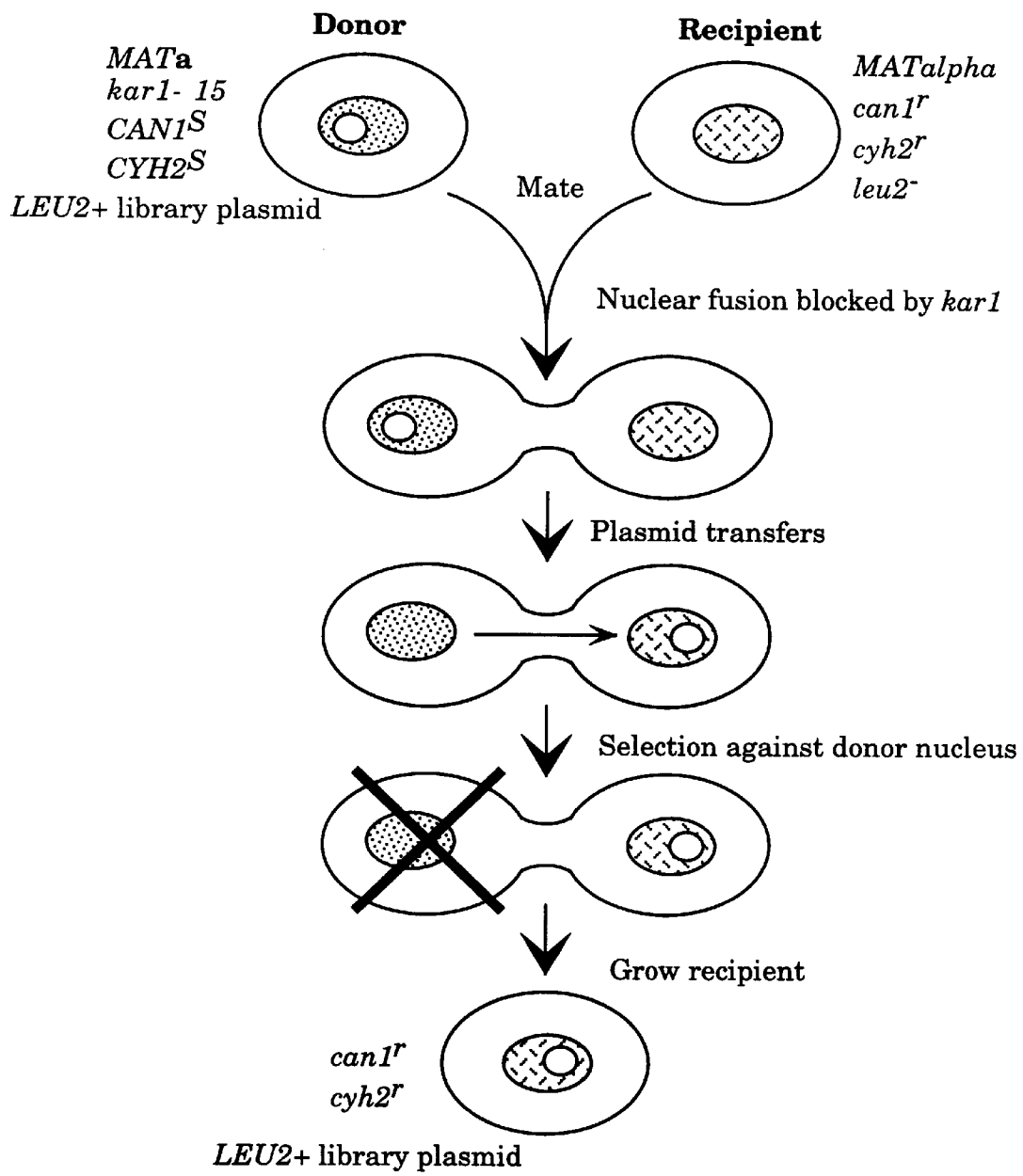

The donor strain that will host the library will contain the following relevant genotype: MATa kar1-$\Delta$15 CAN1$^s$ CYH$^s$ leu2-3,112 his3-11,15 trp1-1 ura3-1. FIG. 8 shows the procedure for kar1-mediated plasmid transfer.

Similar strains have been successfully used for the efficient transfer of yeast artificial chromosomes (YACs) [10]. In such crosses between a donor and recipient, nuclear fusion is rare. However, use of a recessive drug resistant marker, can1 or cyh2, insures that rare nuclear fusions are eliminated by counter-selection. To use this scheme, the recipient strain must be either canavanine resistant or cycloheximide resistant. Since CAN1 is the only gene conferring canavanine sensitivity, can$^r$ mutations can be easily introduced into the recipient strains.

(4) A portable gene disruption library

Figure 9:
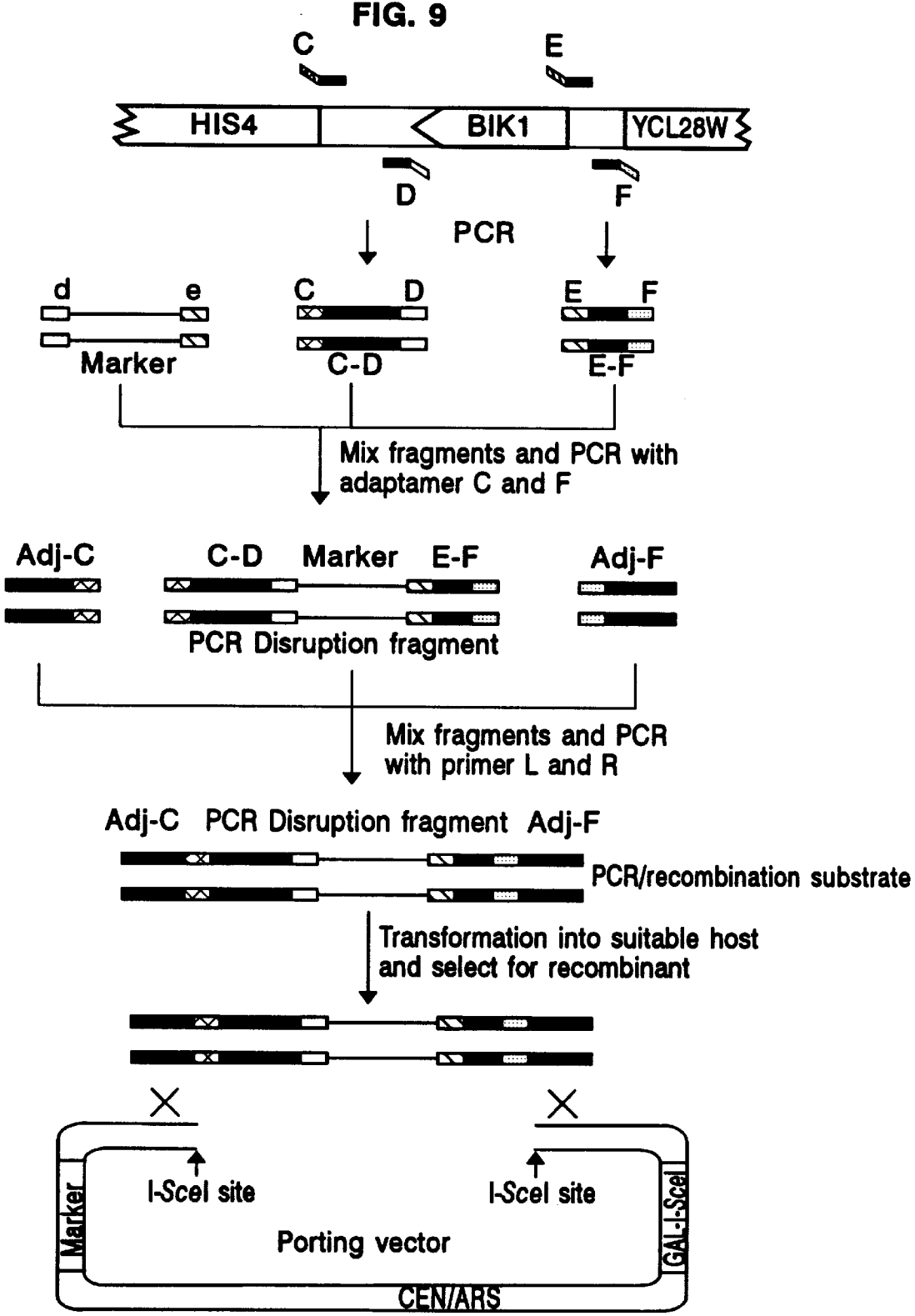

The scheme outlined in FIG. 9 will be used to construct a portable gene disruption library. PCR for the intergenic regions will be the same as that described in FIG. 7. Here the need for alternating C, D and E, F adaptamers becomes apparent. Each ORF is flanked by either C-D and E-F or E-F and C-D. Thus, the disruption marker inserted between these fragment pairs must contain adaptamer d, e ends or adaptamer f, c ends. Fusion PCR among the three fragments results in a disruption fragment in the correct genomic orientation. These fragments can be used to transform yeast directly to disrupt the target genes. The *Kluyveromyces lactis* URA3 gene may be used for selection of disruption [11].

This marker does not efficiently recombine with the endogenous *S. cerevisiae* ura3 gene [12] since they only share 70% identity.

This scheme may be taken one step further to create a portable gene disruption library similar to that described for the promoter fusion library. The disruption fragment will be PCR-fused to the appropriate Adj fragments (Adj-C and Adj-F or Adj-E and Adj-D) and co-transformed with the porting vector into the kar1 donor strain described above with the addition of a gal4 mutation to prevent any expression driven by the GAL1 promoter (see below).

The porting vector contains flanking I-SceI restriction sites, and a galactose-inducible I-SceI gene [13, 14]. This enzyme behaves similarly to the HO endonuclease [15]. The advantage over HO is that this rare restriction site does not exist within the yeast nuclear genome (see FIG. 10). After kar1-mediated transfer of the disruption plasmid into the recipient, the I-SceI gene is induced, the disruption fragment is released and homologous recombination occurs leading to a precise chromosomal gene disruption (see FIG. 11). In the case of essential genes, the viability after induction will be very low.

Figure 10:
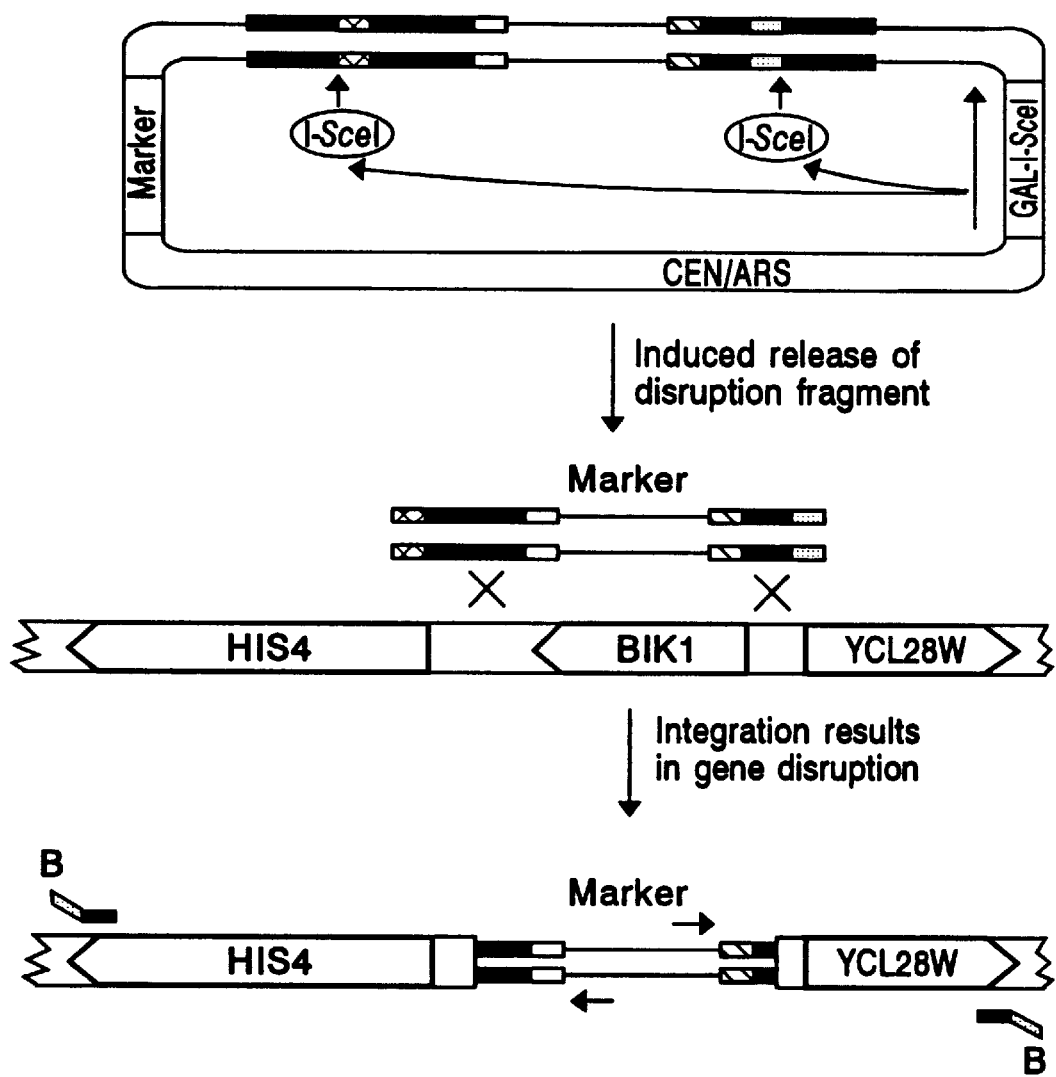
Figure 11:
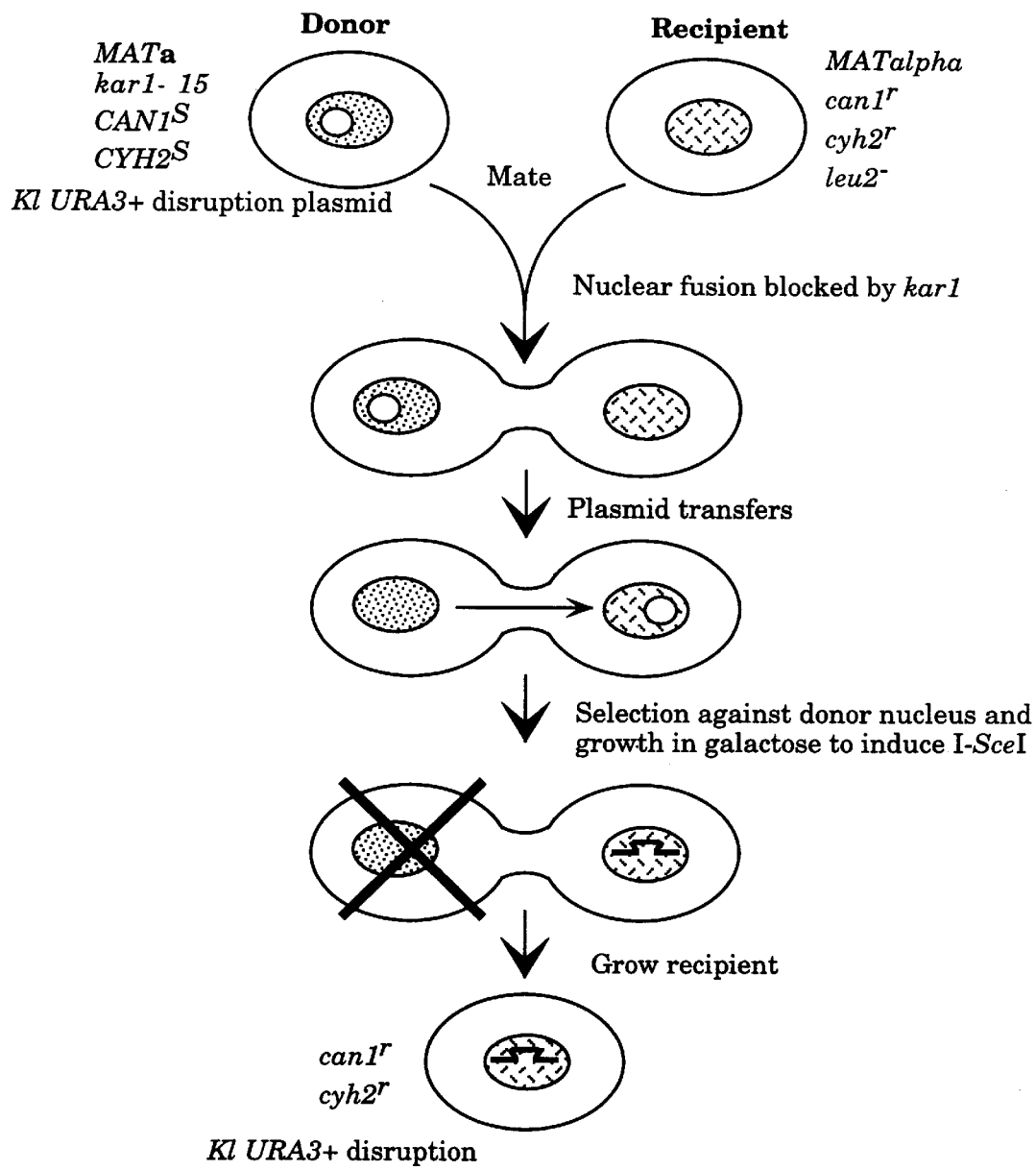
Figure 12:
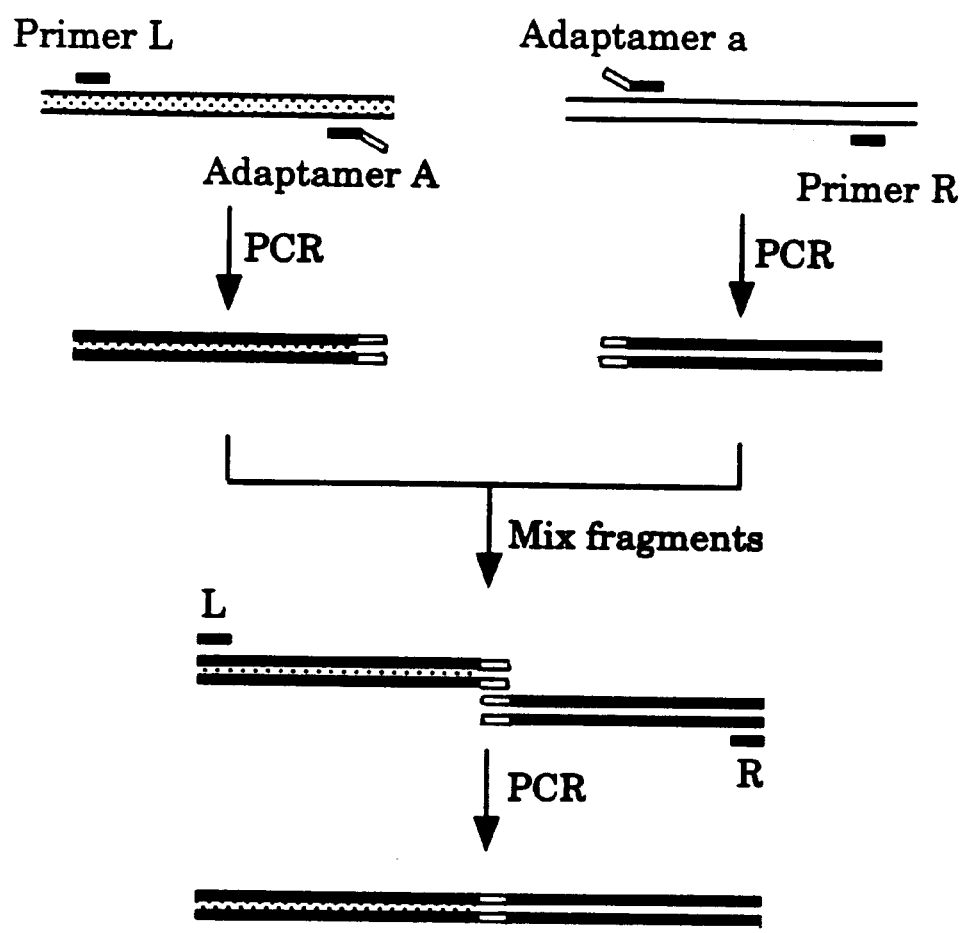
Figure 13:
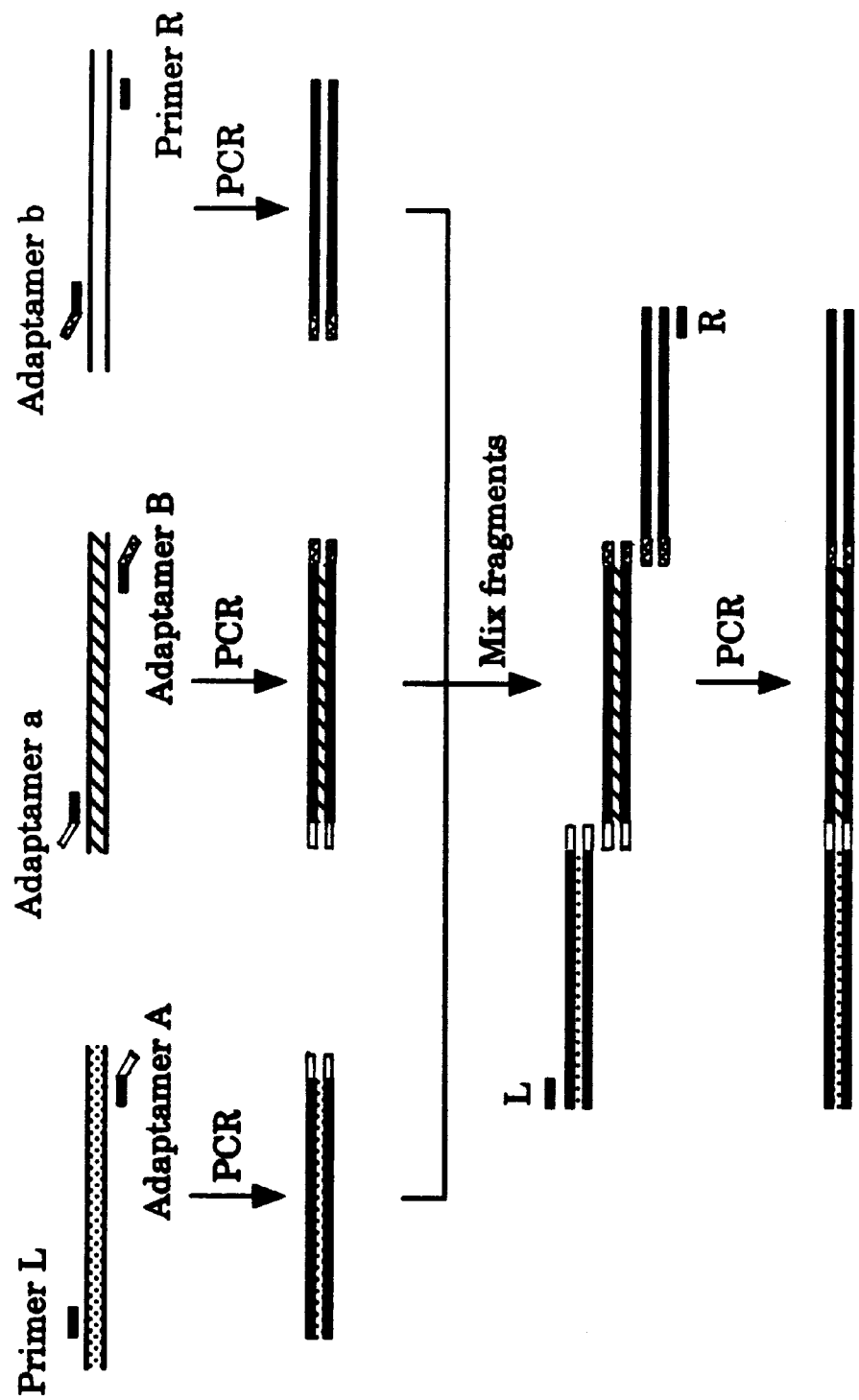

To verify that the gene disruption library in the donor strain is valid, the library may be transferred into a wild type laboratory strain (W303) [16] and examination of the disruptants may be carried out. From previous work, it would be known to one of ordinary skill in the art which genes on chromosome V are essential and they should not grow on galactose. For the others, primers within the disruption marker may be used and the closest adaptamer (A or B in FIG. 3) from either adjacent gene (FIG. 10). Only correct integrations will give the predicted product.

REFERENCES

1. Orr-Weaver, T. L., J. W. Szostak, and R. J. Rothstein, *Yeast transformation: a model system for the study of recombination.* Proceedings of the National Academy of Sciences of the United States of America, 1981. 78(10): p. 6354–8.
2. Rothstein, R. J., *One-step gene disruption in yeast.* Methods in Enzymology, 1983. 101: p. 202–11.
3. Bendixen, C., S. Gangloff, and R. Rothstein, *A yeast mating-selection scheme for detection of protein—protein interactions.* Nucleic Acids Research, 1994. 22(9): p. 1778–9.
4. Fischer, S. G., et al., *A high-resolution annotated physical map of the human chromosome 13q12–13 region containing the breast cancer susceptibility locus BRCA2.* Proceedings of the National Academy of Sciences of the United States of America, 1996. 93(2): p. 690–4.
5. Kunes, S., D. Botstein, and M. S. Fox, *Synapsis-mediated fusion of free DNA ends forms inverted dimer plasmids in yeast.* Genetics, 1990. 124(1): p. 67–80.
6. Ma, H., et al., *Plasmid construction by homologous recombination in yeast.* Gene, 1987. 58(2–3): p. 201–16.
7. Gangloff, S., et al., *The yeast type I topoisomerase Top3 interacts with Sgs1, a DNA helicase homolog: a potential eukaryotic reverse gyrase.* Molecular & Cellular Biology, 1994. 14(12): p. 8391–8.
8. Fields, S. and O. Song, *A novel genetic system to detect protein-protein interactions.* Nature, 1989. 340(6230): p. 245–6.
9. Chalfie, M., et al., *Green fluorescent protein as a marker for gene expression.* Science, 1994. 263(5148): p. 802–5.
10. Spencer, F., et al., *Yeast kar1 mutants provide an effective method for YAC transfer to new hosts.* Genomics, 1994. 22(1): p. 118–26.
11. Shuster, J. R., D. Moyer, and B. Irvine, *Sequence of the Kluyveromyces lactis URA3 gene.* Nucleic Acids Research, 1987. 15(20): p. 8573.
12. Rose, M., P. Grisafi, and D. Botstein, *Structure and function of the yeast URA3 gene:* expression in *Escherichia coli.* Gene, 1984. 29(1–2): p. 113–24.
13. Plessis, A., et al., *Site-specific recombination determined by I-SceI, a mitochondrial group I intron-encoded endonuclease expressed in the yeast nucleus.* Genetics, 1992. 130(3): p. 451–60.
14. Choulika, A., et al., *Induction of homologous recombination in mammalian chromosomes by using the I-SceI system of Saccharomyces cerevisiae.* Molecular & Cellular Biology, 1995. 15(4): p. 1968–73.
15. Kostriken, R., et al., *A site-specific endonuclease essential for mating-type switching in Saccharomyces cerevisiae.* Cell, 1983. 35(1): p. 167–74.
16. Thomas, B. J. and R. Rothstein, *Elevated recombination rates in transcriptionally active DNA.* Cell, 1989. 56(4): p. 619–30.

What is claimed is:

1. A method for generating a directed, recombinant fusion nucleic acid molecule which comprises:
   (A) contacting a first pair of single-stranded primers with a first strand and a second strand of a first nucleic acid molecule and a second pair of single-stranded primers with a first strand and a second strand of a second nucleic acid molecule under hybridization conditions, wherein the primers are suitable for use in a polymerase chain reaction, and
      (i) the first primer of the first pair of primers comprises a sequence that is homologous to the first strand of the first nucleic acid molecule;
      (ii) the second primer of the first pair of primers comprises a 3' sequence that is homologous to the second strand of the first nucleic acid molecule and a 5' sequence;
      (iii) the first primer of the second pair of primers comprises a 3' sequence homologous to the first strand of the second nucleic acid molecule and a 5' sequence that is complementary to the 5' sequence of the second primer of the first pair of primers, and
      (iv) the second primer of the second pair of primers comprises a sequence that is homologous to the second strand of the second nucleic acid molecule;
   (B) amplifying the first nucleic acid molecule with the first pair of primers and the second nucleic acid molecule with the second pair of primers under amplification conditions, separately;
   (C) mixing the amplification products from step (B) and the first primer of the first pair of primers and the second primer of the second pair of primers under hybridization conditions;
   (D) amplifying the hybridized molecules of step (C) under amplification conditions so as to generate a directed, recombinant fusion nucleic acid molecule.

2. The method of claim 1, wherein the method is repeated and the directed, recombinant fusion nucleic acid molecule generated comprises another first nucleic acid molecule.

3. The method of claim 1, wherein the first nucleic acid molecule comprises a cDNA molecule, a genomic nucleic acid molecule, a mitochondrial nucleic acid molecule, a chromosomal nucleic acid molecule, a synthetic nucleic acid molecule or an extra-chromosomal nucleic acid molecule.

4. The method of claim 1, wherein the first nucleic acid molecule is derived from an mRNA, a single-stranded DNA, a biological sample or a single-stranded cDNA.

5. The method of claim 4, wherein the biological sample comprises cerebrospinal fluid, blood, plasma, ascites fluid, tissue, urine, sputum, feces, hair, amniotic fluid, saliva, lung lavage, or cell extracts.

6. The method of claim 1, wherein each primer comprises from about 4 nucleotides in length to about 200 nucleotides in length.

7. The method of claim 1, wherein each primer comprises from about 25 nucleotides in length to about 80 nucleotides in length.

8. The method of claim 1, wherein the second nucleic acid molecule is synthesized de novo.

9. A method for generating a directed, recombinant fusion nucleic acid molecule capable of cross-over recombination which comprises:

(A) contacting
  (i) a first pair of single-stranded primers with a first strand and a second strand of a first nucleic acid molecule, and
  (ii) a first single-stranded primer of a second pair of primers with a second nucleic acid molecule having two ends, wherein a first end is homologous to a portion of a fourth double-stranded nucleic acid molecule;
  (iii) a second single-stranded primer of the second pair of primers with a third nucleic acid molecule having two ends, wherein a first end is homologous to a second portion of the fourth double-stranded nucleic acid molecule, wherein the first and second pair of primers are suitable for use in a polymerase chain reaction, and
    (a) the first primer of the first pair comprises a 3' sequence that is homologous to the first strand of the first nucleic acid molecule and a 5' sequence that is homologous to the second end of the second double-stranded nucleic acid molecule;
    (b) the second primer of the first pair of primers comprises a 3' sequence that is homologous to the second strand of the first nucleic acid molecule and a 5' sequence that is homologous to the second end of the third double-stranded nucleic acid molecule;
    (c) the first primer of the second pair of primers comprises a sequence that is homologous to a first strand within the first end of the second nucleic acid molecule, and
    (d) the second primer of the second pair of primers comprises a sequence that is homologous to the second strand within the first end of the third nucleic acid molecule;
(B) amplifying the first nucleic acid molecule with the first pair of primers, and the second and third nucleic acid molecules with the second pair of primers under amplification conditions so as to generate a directed, recombinant fusion nucleic acid molecule capable of cross-over recombination with the fourth double-stranded nucleic acid.

10. The method of claim 9, wherein the method is repeated and the directed, recombinant fusion nucleic acid molecule generated comprises another first nucleic acid molecule.

11. The method of claim 9, wherein the first nucleic acid molecule comprises a cDNA molecule, a genomic nucleic acid molecule, a mitochondrial nucleic acid molecule, a chromosomal nucleic acid molecule, a synthetic nucleic acid molecule or an extra-chromosomal nucleic acid molecule.

12. The method of claim 9, wherein the first nucleic acid molecule is derived from an mRNA, a single-stranded DNA, a biological sample or a single-stranded cDNA.

13. The method of claim 12, wherein the biological sample comprises cerebrospinal fluid, blood, plasma, ascites fluid, tissue, urine, sputum, feces, hair, amniotic fluid, saliva, lung lavage, or cell extracts.

14. The method of claim 9, wherein the fourth nucleic acid molecule comprises a replicable vector.

15. The method of claim 14, wherein the replicable vector comprises a retroviral vector, a phage vector, an expression vector, a self-replicating vector, a viral vector, a plasmid vector, a phagemid vector, or a YAC vector.

16. The method of claim 9, wherein each primer comprises from about 4 nucleotides in length to about 200 nucleotides in length.

17. The method of claim 9, wherein each primer comprises from about 25 nucleotides in length to about 80 nucleotides in length.

18. The method of claim 9, wherein the second and the third nucleic acid molecules are synthesized de novo.

19. A method for generating a directed, recombinant fusion nucleic acid molecule which comprises:
(A) contacting
  (i) a first pair of single-stranded primers with a first strand and a second strand of a first nucleic acid molecule;
  (ii) a second and a third pair of primers with a second nucleic acid molecule having a first strand and a second strand, wherein the primers are suitable for use in a polymerase chain reaction, and
    (a) the first primer of the first pair comprises a 3' sequence that is homologous to the first strand of the first nucleic acid molecule and a 5' sequence;
    (b) the second primer of the first pair of primers comprises a 3' sequence that is homologous to the second strand of the first nucleic acid molecule and a 5' sequence;
    (c) the first primer of the second pair of primers comprises a sequence that is homologous to the second strand of the second nucleic acid molecule;
    (d) the second primer of the second pair of primers comprises a 3' sequence that is homologous to the first strand of the second nucleic acid molecule and a 5' sequence that is complementary to the 5' sequence of the first primer of the first pair of primers;
    (e) the first primer of the third pair of primers comprises a 5' sequence complementary to the 5' sequence of the second primer of the first pair of primers and a 3' sequence homologous to the second strand of the second nucleic acid molecule, and
    (f) the second primer of the third pair of primers comprises a sequence that is homologous to the first strand of the second nucleic acid molecule;
(B) amplifying (1) the first nucleic acid molecules with the first pair of primers and (2) the second nucleic acid molecule with the second and third pairs of primers, so as to generate at least one linear double-stranded nucleic acid product from each reaction;
(C) denaturing the products from step (B) so as to obtain single-stranded products;
(D) contacting the single-stranded products from step (C) with the first primer of the second set of primers and the second primer from the third set of primers, under suitable hybridization conditions, and
(E) amplifying the single-stranded products from step (D) under suitable amplification conditions, so as to generate a fusion nucleic acid molecule.

20. The method of claim 19, wherein cross-over recombination occurs in an appropriate host cell.

21. The method of claim 20, wherein the host cell comprises a yeast cell, a mammalian cell, an E. coli cell, a eukaryotic cell, a prokaryotic cell, a plant cell, an insect cell, a slime mold cell.

22. The method of claim 19, wherein the first nucleic acid molecule comprises a cDNA molecule, a genomic nucleic acid molecule, a mitochondrial nucleic acid molecule, a chromosomal nucleic acid molecule, a synthetic nucleic acid molecule or an extra-chromosomal nucleic acid molecule.

23. The method of claim 19, wherein the first nucleic acid molecule is derived from an mRNA, a single-stranded DNA, or a single-stranded cDNA.

24. The method of claim 19, wherein the second nucleic acid molecule comprises a replicable vector.

25. The method of claim 24, wherein the replicable vector comprises a retroviral vector, a phage vector, an expression vector, a self-replicating vector, a viral vector, a plasmid vector, a phagemid vector, or a YAC vector.

26. The method of claim 19, wherein the fusion nucleic acid comprises an insertion, a deletion a duplication or a mutation in the fusion nucleic acid molecule.

27. A method for generating a directed, recombinant nucleic acid library which comprises:

(A) contacting
- (i) a first pair of single-stranded primers with a first strand and a second strand of a first nucleic acid molecule;
- (ii) a second and a third pair of primers with a second nucleic acid molecule having a first strand and a second strand, wherein the primers are suitable for use in a polymerase chain reaction, and
  - (a) the first primer of the first pair comprises a 3' sequence that is homologous to the first strand of the first nucleic acid molecule and a 5' sequence;
  - (b) the second primer of the first pair of primers comprises a 3' sequence that is homologous to the second strand of the first nucleic acid molecule and a 5' sequence;
  - (c) the first primer of the second pair of primers comprises a sequence that is homologous to the second strand of the second nucleic acid molecule;
  - (d) the second primer of the second pair of primers comprises a 3' sequence that is homologous to the first strand of the second nucleic acid molecule and a 5' sequence that is complementary to the 5' sequence of the first primer of the first pair of primers;
  - (e) the first primer of the third pair of primers comprises a 5' sequence complementary to the 5' sequence of the second primer of the first pair of primers and a 3' sequence homologous to the second strand of the second nucleic acid molecule, and
  - (f) the second primer of the third pair of primers comprises a sequence that is homologous to the first strand of the second nucleic acid molecule;

(B) amplifying (1) the first nucleic acid molecule and the first pair of primers and (2) the second nucleic acid molecule and the second and third pairs of primers, so as to generate at least one linear double-stranded nucleic acid product from each reaction;

(C) denaturing the products from step (B) so as to obtain single-stranded products;

(D) contacting the single-stranded products from step (C) with the first primer of the second set of primers and the second primer from the third set of primers under suitable hybridization conditions, and (E) amplifying the single-stranded products from step (D) so as to generate a fusion nucleic acid molecule under suitable amplification conditions;

(F) mixing the fusion nucleic acid molecule with the second nucleic acid molecule under suitable recombination conditions so as to generate a directed, recombinant nucleic acid library.

28. The method of claim 27, wherein the library is a two-hybrid library, an interaction library, a receptor library, a whole animal library, a tagged library, a chimeric library, a gene fusion library, a promoter trap library, an expression library, or a mutagenesis library.

29. The method of claim 27, wherein the cross-over recombination occurs in an appropriate host cell.

30. The method of claim 29, wherein the host cell comprises a yeast cell, a mammalian cell, an *E. coli* cell, a eukaryotic cell, a prokaryotic cell, a plant cell, an insect cell, a slime mold cell.

31. The method of claim 27, wherein the first nucleic acid molecule comprises a cDNA molecule, a genomic nucleic acid molecule, a mitochondrial nucleic acid molecule, a chromosomal nucleic acid molecule, a synthetic nucleic acid molecule or an extra-chromosomal nucleic acid molecule.

32. The method of claim 27, wherein the first nucleic acid molecule is derived from an mRNA, a synthetic nucleic acid, a single-stranded DNA, or a single-stranded cDNA.

33. The method of claim 27, wherein the second nucleic acid molecule comprises a replicable vector.

34. The method of claim 33, wherein the replicable vector comprises a retroviral vector, a phage vector, an expression vector, a self-replicating vector, a viral vector, a plasmid vector, a phagemid vector, or a YAC vector.

35. A kit for generating a fusion nucleic acid based library which comprises:

(a) a plurality of the single-stranded nucleic acid molecule primers of claim 27;

(b) reagents suitable to carry out a plurality of polymerase chain reactions, and (c) a replicable vector suitable for recombination.

* * * * *

UNITED STATES PATENT AND TRADEMARK OFFICE
CERTIFICATE OF CORRECTION

PATENT NO. : 5,942,422  
DATED : August 24, 1999  
INVENTOR(S) : Rodney Rothstein It is certified that error appears in the above-indentified patent and that said Letters Patent is hereby corrected as shown below:

column 1, line 3 please insert --The invention disclosed herein was made with Government support under NIH Grant No. GM50327. Accordingly, the U.S. Government has certain rights in this invention.-- column 11, line 1 "are" should read --is-- column 11, line 10 "is should read --are-- column 17, line 28 "a" should read --as a-- column 19, line 35 "Augmentmentation" should read --Augmentation-- column 22, line 30 "expoected" should read --expected--

UNITED STATES PATENT AND TRADEMARK OFFICE
CERTIFICATE OF CORRECTION

PATENT NO. : 5,942,422
DATED : August 24, 1999
INVENTOR(S) : Rodney Rothstein

It is certified that error appears in the above-identified patent and that said Letters Patent is hereby corrected as shown below:

```
column 25, line 27 "problem a" should read --
a problem-- column 25, line 50 "the each size" should
read
     --each size-- column 25, line 66 " of ten" should read --
often--
```

Signed and Sealed this

Sixteenth Day of January, 2001

Attest:

Q. TODD DICKINSON

Attesting Officer

Commissioner of Patents and Trademarks